US010743813B2

(12) United States Patent
Nath et al.

(10) Patent No.: US 10,743,813 B2
(45) Date of Patent: Aug. 18, 2020

(54) DIABETES CONTROL USING POSTPRANDIAL FEEDBACK

(71) Applicants: Rattan Nath, West Orange, NJ (US); Shefali Vyas, West Orange, NJ (US)

(72) Inventors: Rattan Nath, West Orange, NJ (US); Shefali Vyas, West Orange, NJ (US)

(*) Notice: Subject to any disclaimer, the term of this patent is extended or adjusted under 35 U.S.C. 154(b) by 0 days.

(21) Appl. No.: 15/065,841

(22) Filed: Mar. 9, 2016

(65) Prior Publication Data

US 2017/0258395 A1  Sep. 14, 2017

Related U.S. Application Data

(63) Continuation-in-part of application No. 14/852,455, filed on Sep. 11, 2015, now abandoned.

(60) Provisional application No. 62/071,044, filed on Sep. 11, 2014, provisional application No. 62/177,905, filed on Mar. 26, 2015, provisional application No. 62/183,267, filed on Jun. 23, 2015.

(51) Int. Cl.
| | |
|---|---|
| *A61B 5/00* | (2006.01) |
| *A61K 31/07* | (2006.01) |
| *A61K 31/59* | (2006.01) |
| *A61K 31/355* | (2006.01) |
| *A61K 31/202* | (2006.01) |
| *A61K 33/06* | (2006.01) |
| *A61K 45/06* | (2006.01) |
| *A61B 5/145* | (2006.01) |
| *A61B 5/1486* | (2006.01) |

(52) U.S. Cl.
CPC .......... *A61B 5/486* (2013.01); *A61B 5/0002* (2013.01); *A61B 5/14517* (2013.01); *A61B 5/14532* (2013.01); *A61B 5/14865* (2013.01); *A61B 5/4277* (2013.01); *A61B 5/4866* (2013.01); *A61B 5/6898* (2013.01); *A61B 5/742* (2013.01); *A61K 31/07* (2013.01); *A61K 31/202* (2013.01); *A61K 31/355* (2013.01); *A61K 31/59* (2013.01); *A61K 33/06* (2013.01); *A61K 45/06* (2013.01); *A61B 2562/0295* (2013.01)

(58) Field of Classification Search
None
See application file for complete search history.

(56) References Cited

U.S. PATENT DOCUMENTS

| | | | |
|---|---|---|---|
| 4,598,089 A | 7/1986 | Hadvary et al. | |
| 5,820,551 A * | 10/1998 | Hill .................. | A61B 5/1486 204/403.04 |
| 6,004,996 A | 12/1999 | Shah et al. | |
| 6,102,672 A | 8/2000 | Doneen et al. | |
| 6,451,783 B1 | 9/2002 | Hadcock et al. | |
| 6,623,698 B2 | 9/2003 | Kuo | |
| 6,756,364 B2 | 6/2004 | Barbier et al. | |
| 6,861,232 B2 | 3/2005 | Schaffar | |
| 7,815,788 B2 | 10/2010 | Schaffer et al. | |
| 7,933,005 B2 * | 4/2011 | MacIntyre ......... | A61B 5/14532 356/39 |
| 8,898,069 B2 | 11/2014 | Hood et al. | |
| 2001/0023324 A1 | 9/2001 | Provonost et al. | |
| 2003/0175992 A1 | 9/2003 | Toranto et al. | |
| 2003/0235858 A1 | 12/2003 | Gopalan et al. | |
| 2005/0196747 A1 | 9/2005 | Stiene | |
| 2006/0036206 A1 | 2/2006 | Yokoyama et al. | |
| 2006/0258918 A1 * | 11/2006 | Burd ................. | A61B 5/14532 600/310 |
| 2007/0036874 A1 | 2/2007 | Zhong | |
| 2007/0053929 A1 | 3/2007 | Funayama et al. | |
| 2008/0020477 A1 | 1/2008 | Pronovost | |
| 2008/0173064 A1 | 7/2008 | Schaffar et al. | |
| 2008/0227210 A1 | 9/2008 | Smith | |
| 2009/0018416 A1 * | 1/2009 | Walker ................ | G01N 21/314 600/316 |
| 2009/0045056 A1 | 2/2009 | Berberich et al. | |
| 2010/0222648 A1 | 9/2010 | Tan | |
| 2012/0230891 A1 | 9/2012 | Meathrel et al. | |
| 2012/0289588 A1 | 11/2012 | Singh | |
| 2013/0079391 A1 | 3/2013 | Maeder et al. | |
| 2013/0316005 A1 | 11/2013 | Senosiain Pelaez et al. | |
| 2014/0004157 A1 | 1/2014 | Anshima et al. | |
| 2014/0337041 A1 * | 11/2014 | Madden ................ | G16H 10/60 705/2 |

(Continued)

OTHER PUBLICATIONS

Vashist, Sandeep Kumar. "Non-invasive glucose monitoring technology in diabetes management: A review." Analytica chimica acta 750 (2012): 16-27.*

(Continued)

*Primary Examiner* — Robert J Yamasaki
(74) *Attorney, Agent, or Firm* — Rattan Nath

(57) ABSTRACT

Disclosed is a postprandial glucose-measuring device for preventing the development of or reversing T2D. Included are methods for using the device as well as better use for invasive and noninvasive glucose meters. Further disclosed are novel exercise-sensitizing compositions useful for managing blood glucose levels in Type-2 diabetics with minimal risk of hypoglycemia. The disclosed glucose meters allow a user to also measure exercise and meal size—all with relatively instant feedback—more effectively than having to track the complexity posed by labels, glycemic index and calories. Also disclosed is integration of glucose-measuring devices with smartphones and health monitoring technology to make possible safe and effective interpretation of postprandial glucose readings by a patient to control or reverse Type-2 diabetes.

11 Claims, 10 Drawing Sheets

(56) References Cited

U.S. PATENT DOCUMENTS

2015/0080345 A1    3/2015    Kandula

OTHER PUBLICATIONS

Colberg et al., Exercise and Type 2 Diabetes: The American College of Sports Medicine and the American Diabetes Association:joint position statement;Diabetes Care, vol. 33, No. 12, Dec. 2010, pp. e147-e167.
Kadoglou et al., 'Beneficial Effects of Combined Treatment With Rosiglitazone and Exercise on Cardiovascular Risk Factors in Patients With Type 2 Diabetes' in Diabetes Care, vol. 30, No. 9, Sep. 2007,pp. 2242-2244.
Torgerson et al., 'XENical in the Prevention of Diabetes in Obese Subjects (XENDOS) Study' in Diabetes Care, vol. 27, No. 1, Jan. 2004, pp. 155-161.
Roy Taylor, 'Type2Diabetes: Etiology and reversibility'; Diabetes Care, vol. 36, Apr. 2013, pp. 1047-1055.
Stephan F E. Praet, Luc J. C. Van Loon 'Optimizing the therapeutic benefits of exercise in Type 2 diabetes', Journal of Applied Physiology Published Oct. 1, 2007 vol. 103 No. 4, 1113-1120.

\* cited by examiner

DIABETES CONTROL USING POSTPRANDIAL FEEDBACK

CROSS-REFERENCE TO RELATED APPLICATIONS

This application claims benefit of U.S. Provisional Application No. 62/071,044, filed Sep. 11, 2014, the U.S. Provisional Application No. 62/177,905, filed Mar. 26, 2015, and U.S. Provisional Application No. 62/183,267, filed Jun. 23, 2015, and the U.S. patent application Ser. No. 14/852,455 filed on Sep. 11, 2015 the contents of which are hereby incorporated by reference.

BACKGROUND

Type-2 diabetes ("T2D") is one of the most common chronic diseases afflicting humans. The hallmark of T2D is abnormally elevated blood glucose levels. Further, dyslipidemia is encountered in many T2D patients. Dyslipidemia typically manifests itself as elevated Low Density Lipoprotein (LDL), depressed High Density Lipoprotein HDL levels and elevated triglyceride levels. About 79 million Americans ages had prediabetes, a predisposition to develop diabetes, about 1.9 million cases of Americans ages were newly diagnosed with T2D adding to the 25.6 million, or 11.3 percent, of Americans with T2D in the United States according to the U.S. Department of Health and Human Services' estimates. As T2D progresses the regulation of blood glucose levels falters to the point of requiring supplemental insulin. Sedentary lifestyles are believed to be responsible for the increase in T2D, but, on the other hand, the conventional wisdom holds that making lifestyle changes is impractical. Thus, T2D is one of the more pressing health problems treated imperfectly by medications.

As to consequences of T2D, PostPrandial HyperGlycemia (PPHG), but not Fasting HyperGlycemia (FHG), appears to independently predict the occurrence of cardiovascular disease (CVD) events. In addition sustained abnormally high glucose levels (Hyperglycemia) are associated with the long term increase in the risk of strokes, blindness, thickening of the skin, dry skin, infections, and the like. Thus, T2D negatively impacts both mortality and quality of life.

Considerable effort has been expended in developing better medications. Most T2D patients are treated with a combination of medications with most combinations exhibiting risk of hypoglycemia. The least risk of hypoglycemia is with excretagogues and carbohydrate digestion/absorption inhibitors—provided they are not combined with other medications. The medications fall in many classes such as (i) secretagogues (e.g., Sulfonylureas and Meglitinide), (ii) insulin sensitizers (also known as Thiazolidinediones), (iii) gluconeogenesis inhibitors (Biguanides and Dipetidyl peptidase-4 inhibitors), (iv) excretagogues (SGLT2 inhibitors), and (v) carbohydrate digestion/absorption inhibitors (alpha glucosidase inhibitors). There are in development medications/devices to control appetite by manipulating satiety etc. and surgical weight loss procedures—that cure T2D in about half of the patients.

For drugs approved for treating T2D, the Food and Drug Administration ("FDA") requires that their labels include language stating that the medication "is indicated as an adjunct to diet and exercise to improve glycemic control in adults with type 2 diabetes mellitus". How this is to be implemented in practice is still an unsolved problem.

Most medication for treating T2D increase the risk of hypoglycemia. For instance, extra exercise, a smaller or missed meal, or an infection can reduce blood glucose levels dangerously when diabetes is controlled primarily with medications. T2D patients may end up in the Emergency Room due to a minor infection—fighting which suddenly may have consumed plasma glucose with replenishment inhibited by their medications resulting in hypoglycemia and a visit to the Emergency Room. Although exercise is recommended, it is not advisable without close supervision in T2D patients due to the risk of hypoglycemia. Effectively exercise is contraindicated for T2D patients being treated with conventional medications—other than the new class of SGLT2 inhibitors. The latter carry the increased risk of urinary infections and possible elevation of creatinine levels. Thus, for most medication combinations levels physicians choose some hyperglycemia to guard against hypoglycemia.

With the possible exception of the glucagon-like peptide 1 analogs and the thiazolidinediones, which lose their effectiveness eventually as well, other antidiabetic medications lose their effectiveness to control hyperglycemia over time. Therefore, in view of the difficulty in achieving optimal glycemic control for T2D patients using current therapies, there is an unmet medical need for new antidiabetic treatments, particularly those that can reverse the irresistible disease progression.

The HbA1c test provides an indication of the average blood glucose levels over about three months to help evaluate the efficacy of a blood glucose control regime. It has become the de facto standard for diagnosis and evaluation of T2D treatments, but this has reduced the utility for T2D patients of sophisticated home glucose measuring instruments other than for confirming the infrequent hypoglycemia events. Naturally, attempts at developing a commercially successful and medically useful non-invasive blood glucose meter, i.e., requiring no skin punctures, have mostly failed because of their difficulty in reliably detecting hypoglycemia. Bodily fluids (such as saliva, sweat, urine, tears) have glucose at about one fiftieth or even less of that in blood/plasma. Thus, for non-invasive glucose meters the unmet challenge has been to accurately and reliably distinguish between about 70 mg/dL, which is the low end of the 'normal' blood glucose levels and about 60 mg/dL, when hypoglycemia sets in and flag 50 mg/dL levels as dangerous due to impairment of cognitive abilities.

U.S. Pat. No. 6,102,872 by Doneen et al. discloses a saliva based glucose measuring instrument. The '872 patent discloses detection of glucose levels in saliva when blood glucose levels were at about 100 mg/dL. U.S. Pat. No. 8,898,069 by Hood et al. discloses additional salivary glucose detection embodiments using a device enclosed in the oral cavity. US Published Patent Application No. US 2014/0197042 A1 by Zhang et al. discloses measurement of salivary glucose with a resolution of about 0.5 mg/dL with a lower limit of detection at about 1.5 mg/dL corresponding to blood/plasma levels of about 100 mg/dL. Saliva based glucose detection is being developed and tested by QUICK LLC. Some noninvasive meters also use combination of spectroscopic techniques, such as the GlucoTrack meter. These, naturally are very expensive compared to the practice of almost giving away meters that use strips—with the revenue from sales of strips providing the required return but need less consumables. With periodic HbA1c measurements dramatically reducing the utility of regular glucose monitoring in T2D patients, in effect, glucose meters are primarily sustained by their use by diabetics, who do need insulin to control their glucose levels.

Unmet remains the medical need for new and, more importantly, effective antidiabetic treatments for T2D to reverse its irresistible progression under the current treatment strategies.

SUMMARY

We have discovered that many fat or fatty acid absorption inhibiting compositions and compounds have an entirely unexpected benefit. They facilitate the use of postprandial exercise as a tool to regulate blood/plasma glucose levels and to even reverse Type-2 Diabetes and make possible the design and use of an entirely different instrument that integrates diet, exercise and glycemic control. These substances have not been reported to synergize with exercise, despite their use for related applications, such as weight loss. Advantageously, this effect does not impair the natural mechanisms for glucose level regulation. Further, since the fat or fatty acid absorption inhibiting compositions of interest are not absorbed by the body to any great extent when taken orally since they simply pass through the digestive track. As a result, they pose minimal risks of causing hypoglycemia—including due to exercise—that accompanies most medications for treating Type-2 diabetes.

The utility of this discovery is in making possible multiple applications, some of which are described next. It, naturally, allows integration of exercise with treatment of Type-2 diabetes with reduced to no risk of hypoglycemia. Further, it allows reduction in doses of conventional drugs used to treat Type-2 diabetes to make the treatment regime safer. They also reduce the calories taken up and reduce the triglycerides levels as well as cholesterol levels, thus reducing the does of hyperglycemia inducing agents such as statins to control cholesterol and lipids.

The Exercise Sensitizers do not necessarily cause or require weight loss as a precondition for treating T2D. However, they are very compatible with weight loss—which is advantageous in the long run.

Further, there is synergy in combining the Exercise Sensitizers with excreatagogues like SGLT2 inhibitors, which facilitate excretion of glucose via kidneys by inhibiting reabsorption of glucose in the upper ureter. This combination allows pancreatic cells to rapidly recover and measurably reverse T2D in as short a time period as three months.

Then, there is made possible an entirely different instrument, a Postprandial Feedback Meter, integrating diet, exercise and glycemic control using glucose level measurements. Such an instrument can be used to build better habits by helping meter meals and exercise for immediate feedback. An immediate advantage is in not having to track the complexity posed by labels, glycemic index and calories in the effort to arrest and even reverse T2D. Further, since glucose levels are generally high in the postprandial period, this makes possible safe use of noninvasive glucose detection since high accuracy at low glucose levels is not needed.

Finally, integration of such an instrument with smartphones will actually allow a user to do something useful with measured glucose levels—i.e., be able to continually evaluate improvements in glycemic control and sufficiency of exercise. The traditional wisdom is that glucose levels in the postprandial period are not useful or interpretable. With Exercise Sensitizers in play, this wisdom is clearly wrong because such glucose levels show predictable and actionable changes in response to postprandial exercise. This enables compliance by developing and maintaining habits and lifestyles for effective blood glucose management while overcoming psychological challenges in combatting Type-2 diabetes.

Thus, disclosed is a postprandial glucose-measuring device useful in preventing the development of or reversing T2D. Included are methods for using the device as well as better use for existing invasive and noninvasive glucose meters. These methods allow drastic reduction or even elimination of many of the oral medications typically used to control T2D, which reduction translates into fewer side-effects. Further disclosed are novel exercise-sensitizing compositions useful for managing blood glucose levels in Type-2 diabetics with minimal risk of hypoglycemia. A useful exercise-sensitizer composition includes one or more of tetrahydrolipstatin (generic name, orlistat), cholestyramine, colestipol, colestimide, colesevelam, and sevelamer, among many fat or fatty acid absorption preventing compositions. Their effectiveness increases markedly in combination with an SGLT2 inhibitor. SGLT2 inhibitors, the systemically absorbed medication in a preferred therapeutic embodiment, may be used to speed up reversal of T2D.

In this description invasive detection of glucose means detection of glucose levels in blood or plasma obtained by pricking a subject with a lancet point or use of a probe inserted by breaking the skin. On the other hand, noninvasive detection of glucose means detection of glucose in a biological fluid like saliva, sweat or tears, obtaining which does not require pricking or breaking the skin. The measurements may be spectrometric, for example, using electromagnetic, thermal/infra-red, and/or ultrasonic signals.

The method further comprises recommending moderate exercise after a meal. The method also may include using a chair or other furniture modified to facilitate exercise in an office, while travelling, say on planes, trains or even in an automobile. Exercising may be by way of a pivotable arm rest, pedals, or a foot rest that also provides adjustable resistance to provide exercise. And, of course, an office chair may also function as a recumbent bike.

These and other aspects are explained further later with the aid of the accompanying figures, a brief description of which follows.

DETAILED DESCRIPTION

Figure 1:
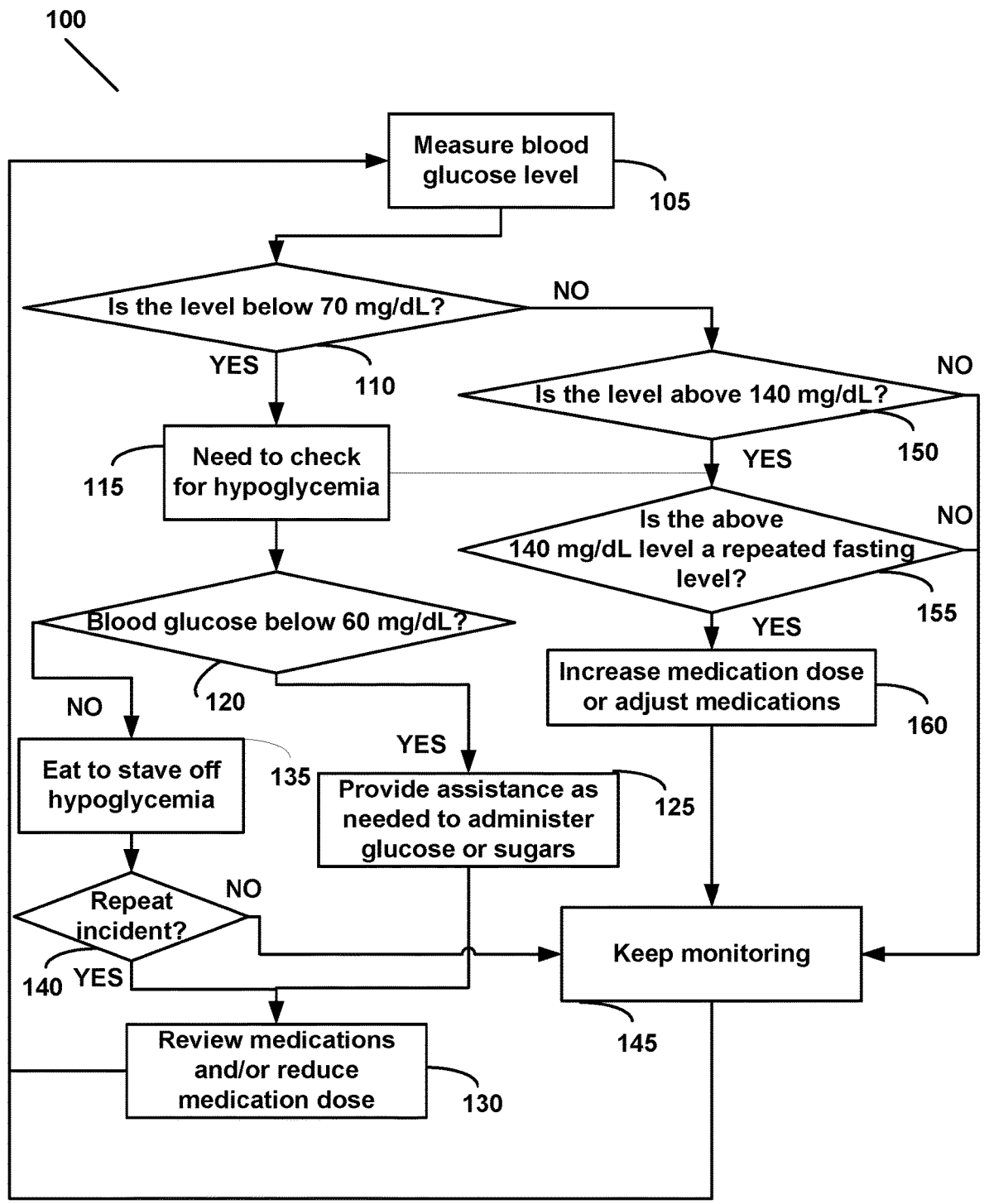
FIG. 1 shows an illustrative prior art method for treating type-2 diabetes.

Contrary to conventional wisdom the changing postprandial glucose levels are a good guide for determining the timing and sufficiency of postprandial exercise to improve glycemic control in subjects at risk of or suffering from T2D. We have made the surprising discovery that fat and fatty acid digestion/absorption inhibitors also act as Exercise Sensitizers in that they enable use of postprandial exercise to adjust glucose levels. Further this integration results in gradually driving down dyslipidemia in addition to improving glycemic control.

This discovery allows for many other applications that were simply not practical under the prior art. The disclosed exercise-sensitizing compositions are useful for managing blood glucose levels in Type-2 diabetics with vastly reduced risk of hypoglycemia when exercising. We also propose a redesign for glucose-measuring devices for use as therapeutic devices for effecting lifestyle changes.

A very useful exercise-sensitizer is tetrahydrolipstatin (orlistat), alone or more preferably in combination with one or more of cholestyramine, colestipol, colestimide, colesevelam, and sevelamer. It is possible to use a pharmaceutically acceptable salt, hydrate, polymorph, solvate, prodrug, enantiomer, or stereoisomer thereof within the scope of this disclosure. This exercise sensitizer combination may be further combined with an SGLT inhibitor, such as one or more of Phlorizin, Canagliflozin ((2S,3R,4R,5S,6R)-2-{3-[5-[4-Fluoro-phenyl)-thiophen-2-ylmethyl]-4-methyl-phenyl}-6-hydroxymethyl-tetrahydro-pyran-3,4,5-triol), Dapagliflozin ((2S,3R,4R,5S,6R)-2-[4-chloro-3-(4-ethoxybenzyl)phenyl]-6-(hydroxymethyl)tetrahydro-2H-pyran-3,4,5-triol), Empagliflozin ((2S,3R,4R,5S,6R)-2-[4-chloro-3-[[4-[(3S)-oxolan-3-yl]oxyphenyl]methyl]phenyl]-6-(hydroxymethyl)oxane-3,4,5-triol), Remogliflozin (5-methyl-4-[4-(1-methylethoxy)benzyl]-1-(1-methylethyl)-1H-pyrazol-3-yl 6-O-(ethoxycarbonyl)-β-D-glucopyranoside), Sergliflozin (2-(4-methoxybenzyl)phenyl 6-O-(ethoxycarbonyl)-β-D-glucopyranoside), and Tofogliflozin ((1S,3'R,4'S,5'S,6'R)-6-(4-Ethylbenzyl)-6'-(hydroxymethyl)-3',4',5',6'-tetrahydro-3H-spiro[2-benzofuran-1,2'-pyran]-3',4',5'-triol hydrate (1:1)), and Sotagliflozin. For the SGLT inhibitors it is acceptable to use an alternative SGLT2 inhibitor or pharmaceutically acceptable salt, hydrate, polymorph, solvate, prodrug, enantiomer, or stereoisomer within the scope of this disclosure.

Looked at another way, the Exercise Sensitizer may be formulated as a supplement to an SGLT inhibitor. Advantageously, such a supplement may comprise not just an Exercise Sensitizer component but also supplemental fat soluble vitamin and nutrients and a source of Calcium. We discovered that such a supplement comprising Vitamin A, Vitamin D, Vitamin E and Calcium—for instance in the form of Calcium Carbonate—is beneficial and synergistic with Exercise Sensitizers, including when combined further with SGLT2 inhibitors and moderate exercise to treat T2D.

Also disclosed is integration of a Postprandial Feedback Meter with smartphones, accessories like watches, and health monitoring technology by making interpretation of glucose readings meaningful and actionable by a patient to control or reverse Type-2 diabetes. This integration also furthers developing and maintaining better habits and lifestyles for effective blood glucose management. Over time the disclosed methods and compositions result in regression of Type-2 diabetes. This integration of methods, devices, compositions, and fine adjustments by the patient also addresses the physiological and psychological challenges in combatting Type-2 diabetes. This is timely since the United States alone has experienced a 60% increase in T2D over the last twenty years, a figure that attests to the unmet nature of problems posed by this chronic condition.

Definitions

Blood/Plasma is the compartment comprising red blood cells and other cells that are carried in plasma that circulates in the body. Glucose concentrations by portable glucose meters are typically reported as those in plasma.

Excretagogues are medications that lead to excretion of excess blood glucose—typically by way of urine—and are usually not Glucose Absorption Inhibitors.

Exercise Sensitizer means a substance that when administered orally is not absorbed by the body to any significant extent but reduces the required intensity, to usually no more than moderate intensity, and duration, usually of ten minutes to an hour though with no real hard limit, of postprandial exercise to reduce postprandial glucose levels into a target range. In effect, this property is a combination of lowering insulin resistance and improving glycemic control but without impairing the natural mechanisms for glucose level regulation. The desirable range for postprandial glucose levels is the normal range for blood/plasma glucose of about 70 mg/dL to 100 mg/dL. Examples of Exercise Sensitizers include fat or fatty acid absorption preventing candidates like Orlistat (also known as tetrahydrolipstatin((S)—((S)-1-((2S,3S)-3-Hexyl-4-oxooxetan-2-yl)tridecan-2-yl) 2-formamido-4-methylpentanoate)), Cetilistat (also known as 2-(Hexadecyloxy)-6-methyl-4H-3,1-benzoxazin-4-one), Lipstatin ([(2S,4E,7E)-1-(3-hexyl-4-oxo-oxetan-2-yl) trideca-4,7-dien-2-yl](2S)-2-formamido-3-methyl-pentanoate), Poly Ethylene Glycol and its lipophilic derivatives, Cholestyramine, Colestipol, Colestimide, Colesevelam, and Sevelamer and pharmaceutically acceptable salts, hydrates, polymorphs, solvates, prodrugs, enantiomers, or stereoisomers thereof.

Gluconeogenesis Inhibitors are medications that inhibit gluconeogenesis, the generation of glucose by the liver.

Carbohydrate Digestion/Absorption Inhibitors are medications that inhibit absorption of glucose, including for instance by interfering with carbohydrate digestion.

Glycemic Control is the ability to control blood/plasma glucose levels, usually within normal ranges for blood/plasma glucose.

Habit Cue means a trigger for initiating a sequences of behaviors or actions—often subconsciously.

Habit Result/Reward means the end result of performing the Habit Routine, absent which the Habit Routine is meaningless.

Habit Routine means the sequence of steps triggered upon encountering Habit Cue.

Hyperglycemia means blood glucose levels about or above 120 mg/dL Hypoglycemia means blood glucose levels about or below 60 mg/dL.

Instructing means promoting use or a method of use by way of product inserts, user manuals, or advertising, such as for a glucose meter or a medication for treating T2D.

Insulin Sensitizers are medications that increase sensitivity to insulin. Examples are medications classified as thiazolidinediones.

Invasive Glucose Detection means the detection of glucose levels in a biological fluid or tissue obtained by a procedure that requires at least breaking the skin.

Noninvasive Glucose Detection means detection of glucose without requiring a puncture to draw a biological fluid or sample.

Postprandial Exercise means exercise undertaken after a meal.

Postprandial Monitoring Device measures glucose following a meal—usually within about three hours following a meal. This time period can be longer in T2D patients since their glucose levels do not come down as fast as those for subjects with normal Glycemic Control.

Saliva means the secretion in the oral cavity by salivary glands. It is often sampled with contamination with food particles if the mouth has not been thoroughly cleaned.

Secretagogues are medications that cause increased secretion of insulin. Examples are medications classified as sulfonyl ureas.

SGLT inhibitors mean compounds that effectively block Sodium-Glucose Transport proteins. There are several types of SGLT inhibitors, with the primary ones being SGLT1 and SGLT2. SGLT2 inhibitors are found mostly in the urinary system, where they remove glucose from urine and pump it back into the body such that normal urine has almost no glucose. Examples are SGLT2 inhibitors like Canagliflozin that work by allowing glucose to be excreted in urine.

Target Range means the glucose level or range into which glucose levels should be reduced by a subject according to general recommendations or a specific recommendation by a physician, but not including blood/plasma glucose levels of less than about 70 mg/dL or higher than about 140 mg/dL.

Traditional Medications means medications such as (i) secretagogues (e.g., Sulfonylureas and Meglitinide), (ii) insulin sensitizers (also known as Thiazolidinediones), (iii) gluconeogenesis inhibitors (Biguanides and Dipetidyl peptidase-4 inhibitors) used to treat T2D that are capable of driving the system into hypoglycemia.

Illustrative Embodiments

Here we first discuss the broad outlines of our approach followed by a discussion of the Postprandial Feedback Meter designs, novel compositions that synergize with the use of the device and the novel methods disclosed for managing T2D. With these realistically reversal of or avoidance of T2D can be reasonably be expected in a large number of at risk subjects—such as those with newly diagnosed T2D or those at risk of developing T2D. Then we describe the a Postprandial Feedback Meter design and its details that address both safety and operational aspects. The novel compositions are addressed next with some discussion on this new category of medications defined by their ability to sensitize a subject to exercise—by making the glucose levels responsive to exercise as well as making exercise less cumbersome with the aim to reduce glucose levels. Finally we discuss the method taken as a whole to describe how and why it helps form useful habits and bring about lifestyle changes.

We also present results of a reversal of T2D over about three months in a subject using the described methods as proof of concept for our approach. It should be noted that while much of the principles supporting this approach are included in the detailed description, this theory is not intended to act as a limitation on the scope of the claims.

Exemplary Example of Prior Art

FIG. 1 is an illustrative prior art method 100 for managing T2D. At step 105 blood/plasma glucose is directly measured. Alternatively it may be measured indirectly using HbA1c or by detecting glucose in the urine, or be inferred from excessive thirst and the like. In all cases a blood/plasma glucose test is usually administered at some point to initiate treatment. If the blood/plasma glucose level is below about 70 mg/dL at step 110, then, at step 115, likelihood of hypoglycemia is evaluated. Control passes to step 120, during which if blood/plasma glucose level is below about 60 mg/dL then control passes to step 125, during which assistance is provided, for instance by administering sugars or glucose. Control then passes to step 130, during which medications and other factors are reviewed and adjusted to avoid future episodes of hypoglycemia. On the other hand if glucose levels in step 120 are not below about 60 mg/dL, then the patient has low blood glucose but is able to take actions, such as eat or ingest sugars in step 135 to stave off possible hypoglycemia. Control passes to step 140 for evaluation if possible hypoglycemia is a repeat incident and the like. Control passes to step 130 for a review and adjustment of medications, which naturally leads back to the next blood glucose measurement in step 105.

During step 110, if the glucose levels are higher than 70 mg/dL, control passes to step 150 for evaluation if it is higher than 140 mg/dL. If so, control passes to step 155 for evaluation if this is a repeated fasting glucose level. If the fasting glucose level has repeatedly been high, as determined in step 155, medications are adjusted in step 160 to better control glucose levels. This adjustment may include the use of insulin if oral or other medications fail. Eventually most medications fail as the disease progresses and insulin is required to control T2D in many patients. Control then passes to step 145 to keep monitoring the patient and the disease progression with control passing to step 105. If at step 150, glucose levels are below 140 mg/dL or at step 155 the high glucose level is an outlier, then control goes to step 145 for continued monitoring of the patient and disease and control returns to step 105.

Not all deviations of blood glucose levels have similar effects and some deviations are more concerning than others. PostPrandial HyperGlycemia (PPHG), but not Fasting HyperGlycemia (FHG), appears to predict the occurrence of cardiovascular disease (CVD) events. In addition sustained abnormally high glucose levels are associated with the risk of strokes, blindness, thickening of the skin, dry skin, infections, and the like. But in the short term, too low a blood glucose level, termed hypoglycemia, is life threatening. As a result, in treating diabetes if blood glucose levels are controlled using Traditional Medications to be very close to the normal levels, the risk of hypoglycemia and of PPHG spikes increases as does overall mortality. Therefore, physicians err on the side of allowing hyperglycemia rather than hypoglycemia when prescribing medications. Unsurprisingly, sustained hyperglycemia makes T2D a progressive disease that is effectively impossible to reverse by medications alone.

It is known that increased body weight and obesity are risk factors for developing T2D. While targeting obesity may be sufficient for treating T2D, we realized that it is not a necessary condition or even a useful target in and of itself. We have therefore treated weight loss as a distinct problem that is related to that of improving glycemic control. Thus, while both weight loss and improved glycemic control may be achievable in many subjects, weight loss is not required for better glycemic control or even for reversing T2D. The primary focus should be on improving glycemic control.

A desirable T2D treatment program preferably should (i) minimize the risk of hypoglycemia; facilitate exercising; (ii) reduce the postprandial glucose and/or triglyceride spikes;

(iii) be easy to implement; (iv) reduce sustained hyperglycemia by enabling close to normal regulation of blood/plasma glucose; (v) provide cues and results to establish habitual compliance; and (vi) reverse or at least stop the progression of or towards T2D.

Hypoglycemia is the major risk facing T2D patients using medications to control their plasma glucose levels. Most of the medications for treating T2D—including the standard of care treatment of initiating treatment with metformin (a biguanide)—carry a significant risk of facilitating hypoglycemia. An increase in glucose usage can result in hypoglycemia in T2D patients, which can quickly escalate to confusion, coma, and cognitive decline, and if not treated immediately, it can even result in death. For instance, in seven cases investigated by the Food and Drug Administration (FDA), in hospital settings patients, most of them diabetic, were dosed with a maltose containing fluid which shows up as misleadingly elevated glucose readings in portable glucose readers using the glucose dehydrogenase pyrroloquinolinequinone (GDH-PQQ) methodology. As a result they were treated with insulin for hyperglycemia, which instead resulted in causing hypoglycemia and several deaths as insulin increased the utilization of glucose dramatically.

The other challenge in treating T2D is in improving compliance since glucose spikes are not sensed by the patient. As a result there is no trigger for doing something to combat rising or high glucose levels. Further, as soon as patients feel even slightly well, many stop even the task of regularly taking their medications leave alone exercising regularly. Many approaches to correct this have been tried. Some tested approaches include reminders for exercise, keeping logs of meals and food intake, entering blood glucose readings in a database to allow calculation of effectiveness of the medications and lifestyle factors in treating T2D etc. Smartphones have been pressed into service but have been in disfavor for continuous monitoring of glucose levels due to concerns that it is impractical for such programs to meaningfully interpret the data and would more likely confuse the patients who may unknowingly expose themselves to serious harm. The Diabetes Control and Complications Trial showed that reducing hyperglycemia was beneficial in combatting diabetic retinopathy but subsequent trial showed that tight glucose control with medications increased mortality. Thus, medications by themselves do not offer a viable treatment option.

Our method and Postprandial Feedback Meter overcome these limitations because making measurements in the postprandial stage with postprandial exercise reduces the glucose levels rapidly. Further, the method makes it possible for a patient to make the fine adjustments in blood glucose levels instead of relying on infrequent visits with a physician. Being able to detect the need to exercise or when a meal was too large also provides the cues and results needed for habit formation to improve compliance. The patient can view the short term effects of post-prandial exercise and modify her or his lifestyle. The physician, in this paradigm, tracks HbA1c levels and prescribes the proper use of the Postprandial Feedback Meter together with Exercise Sensitizer and preferably an SGLT2 inhibitor at appropriate doses.

Further, Traditional Medications may be prescribed at lower and far safer doses since they need not bring glucose levels close to normal levels. Instead with the methods disclosed herein the Traditional Medications only need reduce blood glucose levels sufficiently to enable the postprandial exercise in combination with an Exercise Sensitizer to provide meaningful fine control.

Our methods also provide a practical context for implementing noninvasive glucose monitoring. In the post meal context it is preferable to use non-invasive glucose monitoring since there is no appreciable risk of hypoglycemia while the relaxation of the need to invasively obtain blood makes compliance easier. Noninvasive measurement of blood glucose levels after a meal presents almost no risk of missing hypoglycemia because blood glucose levels are uniformly high and are expected to be high. In our methods, these levels are reduced to a desired range only with effort in the form of exercise. In other words, this is when noninvasive detection of glucose is practical and useful. And then, the normal gluconeogenesis machinery steps in to prevent hypoglycemia.

Figure 8:
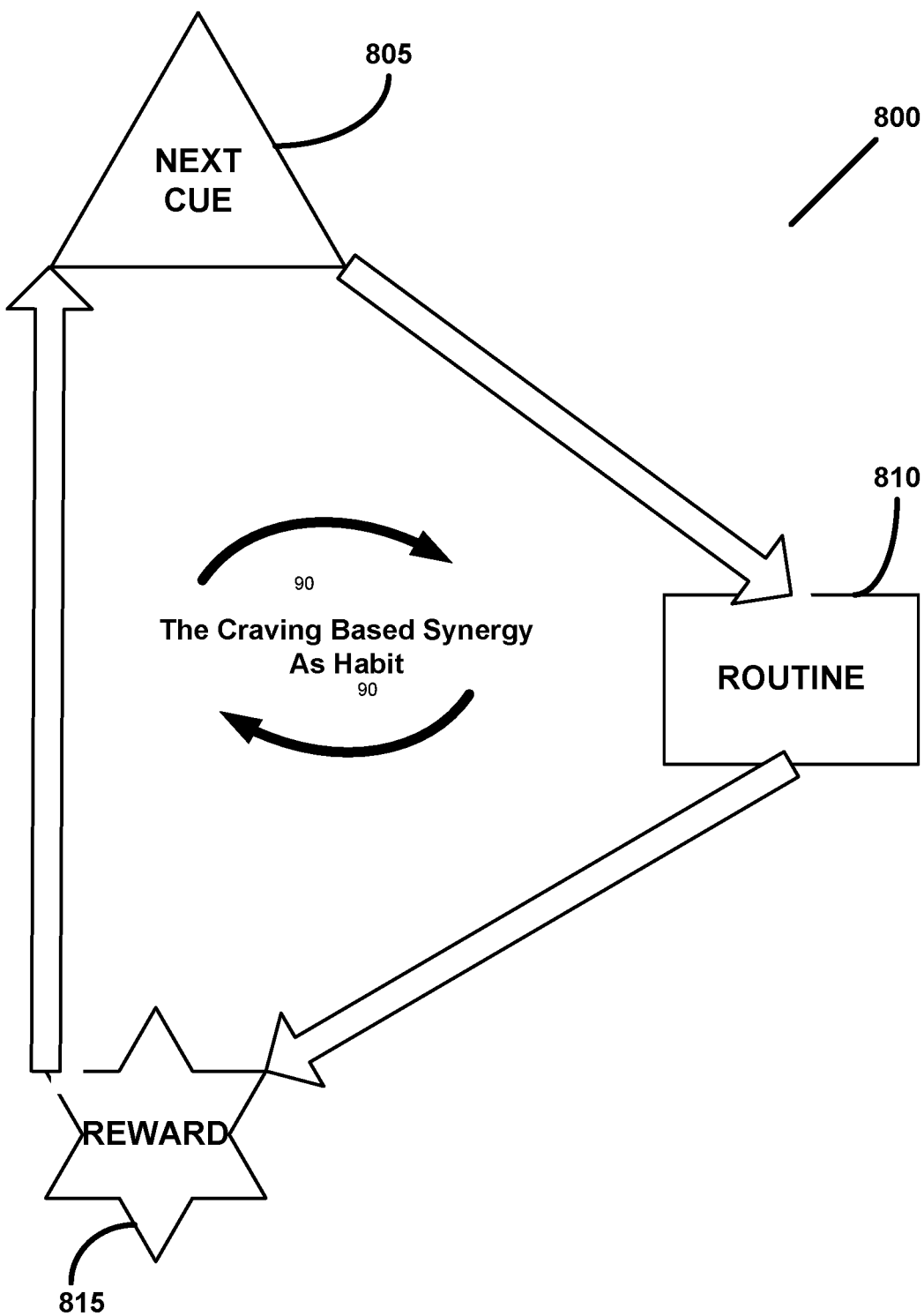
FIG. 8 shows a prior art habit loop showing the development of a craving to execute a routine in response to encountering a cue in order to achieve a result.

FIG. 8 illustrates a prior art habit loop. To inculcate a habit what is required is creating a craving for executing a set of steps upon being presented with a cue. The craving develops if the execution of the steps produces a desirable and immediate result. As an example, for brushing teeth, the Habit Cue is the morning breath and ablutions. In each instance, the steps of brushing include using toothpaste. But the toothpaste in overwhelming instances is minted and provides the minty sensation as the desirable and immediate result of completing the execution of the steps—the Habit Result/Reward. Failure to brush results in missing the expected minty feeling resulting in regular brushing more often than not by most. Thus, in a habit loop a Habit Cue is needed to trigger a set of steps, the Habit Routine, followed by a desirable result, the Habit Result/Reward, making execution of the Habit Routine effortless.

Figure 2:
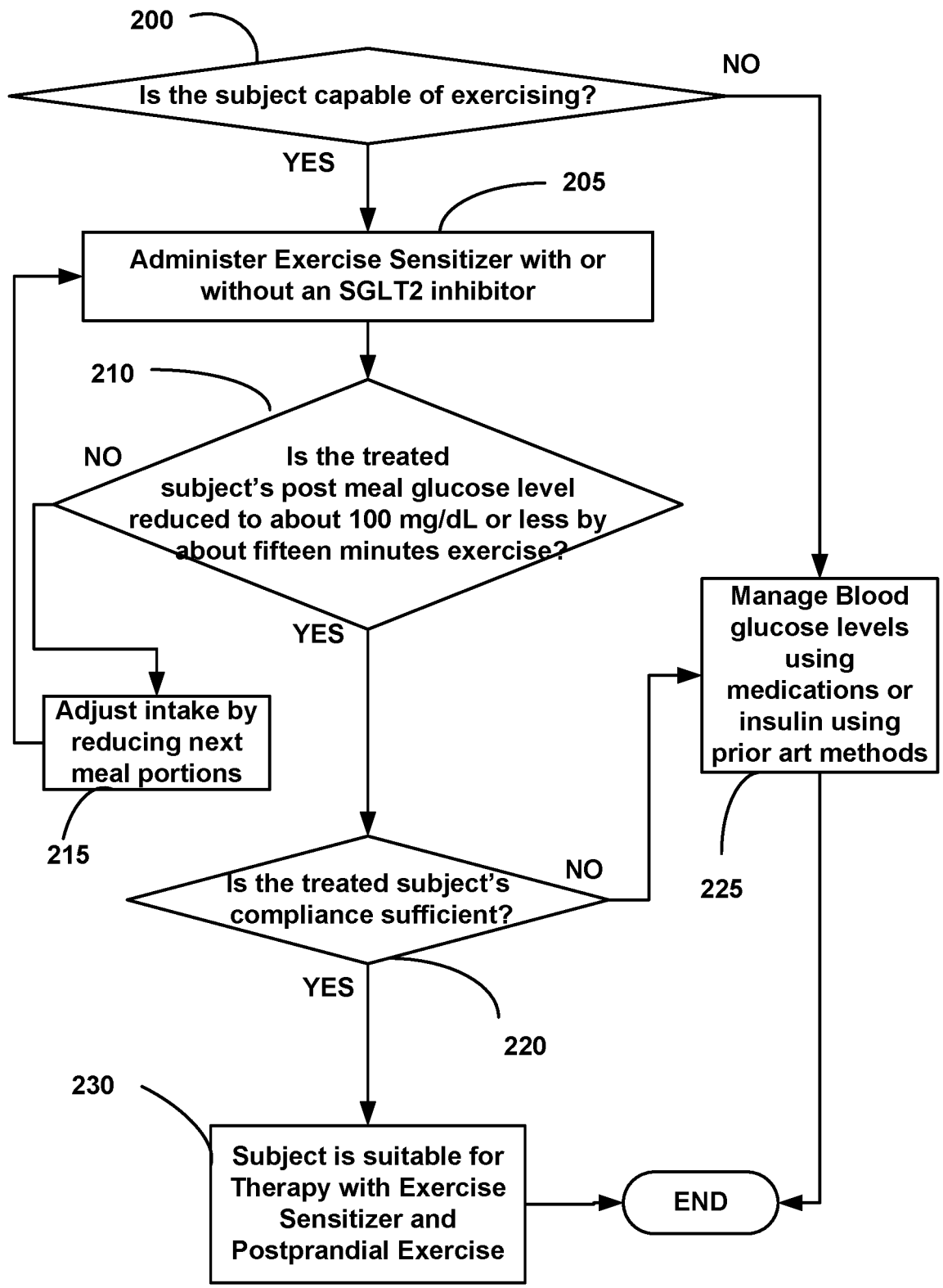
FIG. 2 shows an illustrative method for selecting a subject for postprandial exercise based treatment for Type 2 diabetes.

FIG. 2 shows an illustrative algorithm for deciding if standard of care treatments for T2D is needed to manage blood sugar levels due to psychological or physical impairments that make postprandial exercise impractical. As shown in illustrative FIG. 2, the patient was capable of engaging in exercise. FIG. 2 shows an exemplary algorithm for deciding if a patient can exercise safely. At step 200 the patient is evaluated for factors such as handicaps, CVD or emphysema and the like that would indicate that exercise would cause harm or is impractical. If the subject is capable of exercising control goes to step 205, during which the fasting patient is administered an Exercise Sensitizer—with or without an SGLT2 inhibitor with a meal. For an adult, a dose may be, for instance, about 60 mg. of orlistat as an Exercise Sensitizer. Control then flows to step 210, during which the meal portion size is evaluated. A possible standard may be that with fifteen minutes of exercise blood glucose should drop to less than 100 mg/dL. If the blood glucose does reduce in this manner, then a good therapy has been demonstrated and the routine exits. However, if blood glucose level does not reduce to below about 100 mg/dL, then the meal size is adjusted down in step 215. Control then flows back to step 205 for the next dosing. On the other hand, if the subject does have a reduction in blood glucose levels with postprandial exercise, then control passes to step 220, during which subject's ability to comply is evaluated to ensure it is being tracked. Repeated failures would indicate that T2D should be managed with Traditional Medications as indicated in step 225. For reasonably compliant subjects, then the subject is suitable to benefit from postprandial exercise and Exercise Sensitizers to improve glycemic control in step 230—including with the addition of an SGLT2 inhibitor and lipid soluble vitamins as well as calcium.

Example 1

A 54 year old man was diagnosed with Type 2 DM, dyslipidemia with overweight (BMI 29). He was initially diagnosed to have prediabetes at age of about 35 and then at age=54 was noted to have overt type 2 diabetes. At age 56 he was found to have HbA1c of about 8 with fasting glucose levels of 170 mg/dL. The family history was noteworthy with both parents and sibling having diagnosis of hypertension, T2D and obesity. Physical exam noted BMI 30.2. He had received prescription for metformin and statin upon initial diagnosis to control glucose levels and dyslipidemia but had not continued the therapy in view of being advised of the progressive nature of the disease and being discouraged by the prognosis and the failure to Metformin to sufficiently reduce the blood glucose levels—even with the doubling of the Metformin dose.

Example 2

The patient of Example 1 was encouraged to track glucose levels, including postprandial glucose levels, to observe the effect of postprandial exercise and lifestyle changes. To control triglyceridemia he also started over the counter orlistat at a 60 mg dose daily with a daily multi-vitamin supplement and an additional vitamin D supplement. He had discontinued metformin and statins. Instead close monitoring of blood glucose levels was undertaken.

Figure 3:
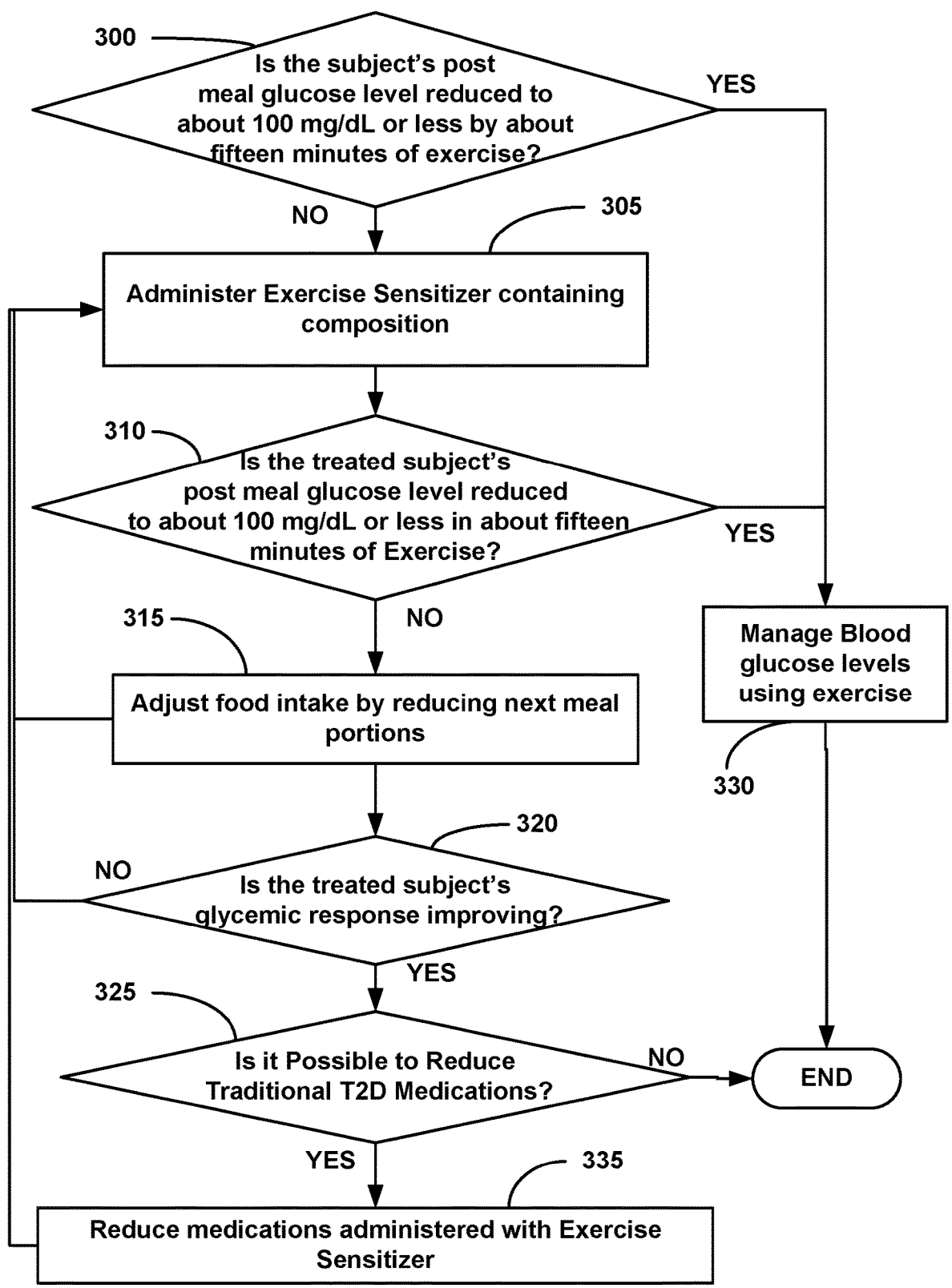
FIG. 3 shows an illustrative method for adjusting a meal size and determine Exercise Sensitizer based reduction in Traditional Medication levels.

Postprandial exercise was initiated by the patient sua sponte after each meal as he sought to adjust the meals to control blood glucose levels. FIG. 3 shows how a hypothetical subject may adjust a diet using our method to bring about lifestyle changes. At step 300 an evaluation is made as to whether a subject's postprandial glucose level drops to about 100 mg/dL or less using about fifteen minutes of exercise. If the glucose level does not drop to about 100 mg/dL, control flows to step 305, during which one or more Exercise Sensitizers are administered. Control flows to step 310 during which an evaluation is made as to whether a subject's postprandial glucose level drops to about 100 mg/dL or less using about fifteen minutes of exercise. If this is ineffective control flows to step 315 during which the portion sizes are adjusted lower. Control then flows to step 320 during which the glycemic response is evaluated for improvements. A failure to detect persistent improvement leads back to step 305 for the next administration of Exercise Sensitizers— presumably the next day. On the other hand, if the glycemic response does improve then control flows to step 325 during which Traditional Medications, if any, for treating T2D are evaluated for reduction. If no reduction is possible control because there are no Traditional Medications being administered then the control flows to step 330 for management of blood glucose levels using postprandial exercise. If a reduction is possible then control flows to step 335 for effecting a reduction or even elimination of the medications. Control flows back to step 305 for the dosing next day. It should be noted that at step 300 if the blood glucose level is below 100 mg/dL, control flows to step 330 for continued management of blood glucose levels using postprandial exercise. This is useful for those with prediabetes since it ensures it is tracked early and corrected using the minimal treatment described herein.

Further, it should be noted that the time period of fifteen minutes is illustrative. It is possible to use a Postprandial Feedback Meter to decide when sufficient exercise has been undertaken based on the time at which glucose levels drop into the normal range or a specified range like at or below 100 mg/dL in this exemplary method. This makes the method flexible and useful for physician treating patients so that they can guide the patient with a demonstration of the actual effects of portion control and exercise in as little as a single session of maybe an hour. Of course, if more time is needed to arrive at the desired adjustments allowed for by the illustrative exemplary method.

In Example 2, when using orlistat at 60 mg daily, the patient noticed that blood glucose levels reduced to a level of about 90 to 100 mg/dL, which is in the normal range, after a modest meal with a brisk walk after eating. The blood glucose levels stayed below 100 mg/dL for several hours. This shows the efficacy of Exercise Sensitizers in allowing a management of glucose levels using exercise instead of the standard of care treatments for T2D in which exercise cannot and should not be taken up willy-nilly due to the risk of hypoglycemia. Effectively exercise is contraindicated in standard of care treatments for T2D due to the use of medications that can drive the glucose levels too low.

Example 3

The 56 year old subject of Example 2 exercised in the postprandial state within about an hour and a half after eating but was not treated with Traditional Medications or any Exercise Sensitizer for more than a week. Following exercise, blood/plasma glucose levels dropped by about 20 mg/dL but further drops required intense exercise and the blood glucose levels stayed stubbornly high.

The descriptions in the art are consistent with this observation in that exercise required to reduce blood glucose levels is relatively intense. It is against this background that the role of Exercise Sensitizers in making even a brisk walk sufficient for reducing blood glucose levels becomes even more significant. As shown in Examples 10, 11 and 12, the level of exercise is relatively low intensity and does not take more time than what has been observed for intense exercise in the prior art using folks in prime physical shape.

Example 4

A 56 year old subject with T2D with fasting glucose levels of over 140 mg/dL was treated with 60 mg Orlistat. The subject undertook exercise in a postprandial state within about an hour and a half after eating. Blood/plasma glucose levels dropped sharply to the normal range. Subsequently the blood/plasma glucose levels rose but stabilized for the next several hours at about 95 to 110 mg/dL, well below the high levels until the next meal indicating hysteresis in blood glucose levels when adjusted with postprandial exercise.

Example 5

A 56 year old subject with T2D with starting fasting glucose level of about 140 mg/dL to 160 mg/dL and HbA1c of about 8 was treated with Orlistat. In one aspect, the 56 year old subject with T2D was treated with 60 mg Orlistat and exercised in a fasting state. Presumably as gluconeogenesis kicked in, the blood/plasma glucose level increased or remained steady in the high range over fifteen to thirty minutes instead of the usual decline observed with postprandial exercise. Thus, the use of Orlistat did not prevent the rise in blood glucose levels but in the postprandial state it allows a reduction in glucose levels using exercise or other means for reducing glucose levels. Although not intending to be bound by theory, one factor may be the natural inhibition of gluconeogenesis in the postprandial state. In addition, the release of fatty acids or lack thereof may affect the release of cholecystokinin and other downstream effects and thus account for the synergy between the postprandial state and the Exercise Sensitizers.

This result also shows that the risk of hypoglycemia is very low in this regime since gluconeogenesis is not impaired.

Example 6

Over three months to speed up the slow progress the 56 year old subject with T2D with fasting glucose level of about 140 mg/dL and HbA1c of about 7.5 or above was treated with Orlistat at the lowest marketed dose of 60 mg and the lowest dose for either Canafliglozin (100 mg) and Dapagliflozin (5 mg). Postprandial exercise with orlistat reduced triglycerides to about 260 mg/dL from over 500 mg/dL.

An invasive glucose testing meter was used to simulate a post-prandial invasive/noninvasive glucose monitoring device. Specifically a combination of orlistat and a SGLT2 inhibitor (Canafliglozin and Dapagliflozin) was administered. Treatment with orlistat (60 mg) daily alone with some The fasting glucose levels changed and continued to decrease overall over the three months. In combination with postprandial exercise the blood glucose levels dropped to high 70 s or low 80 s (in mg/dL) and then slowly recovered over hours to less than about 100 mg/dL. Over three months the glycemic response improved and eventually reduced the fasting glucose levels to about 95 mg/dL (with some values as low as about 85 mg/dL and no higher than about 100 mg/dL) and the HbA1c to about 6.2 at the end of three months and 6.3 at the end of four months (one additional month).

The results show the surprising result that Type 2 diabetes can be reversed by our methods and compositions relatively easily—an entirely unexpected finding considering the data and experience to date of Janssen (See, JNJ-28431754 (Canagliflozin) NDA 204042 dated Jan. 10, 2013 and titled 'Canagliflozin as an Adjunctive Treatment to Diet and Exercise Alone or Co-administered with Other Antihyperglycemic Agents to Improve Glycemic Control in Adults with Type 2 Diabetes Mellitus). This investigation includes stratification of subjects by HbA1c. The data on page 55 show that for starting HbA1c below 8 the observed improvement was less than 0.8 even with 300 mg/day of Canagliflozin per day over as long as 52 weeks. The usual improvement in HbA1c values expected with SGLT2 inhibitors is about 0.7 to 1.0. We observed improvements for the combination of 100 mg/day of Canagliflozin with 60 mg/day of orlistat and postprandial exercise of about 1.3 in HbA1c as well as reduction in fasting glucose levels to normal ranges in this short time period. It is reasonably expected that these efforts will lead to further reductions in HbA1c with time—our observations covered three months for this experiment while other studies have been over almost a year but have less favorable outcomes, which is evidence of synergy in our compositions and methods.

The fasting glucose levels were obtained using a portable glucose meter while the fasting glucose (again to check the meter and strip accuracy) and HbA1c were determined using laboratory tests that included a lipid panel. The subject did not use statins at any point in this treatment but did have nutritional supplements like daily vitamins and calcium. Also the subject could not be fully compliant—many meals were not followed by exercise. The treatment with Exercise Sensitizer and SGLT2 inhibitor was adhered to strictly. Still, the triglyceride levels dropped to 260 and eventually to about 220 from about 500. The BMI did not change appreciably and stayed at about 30. Thus, the approach described herein performs far better than standard of care by identifying a true synergy that is not predictable from isolated pieces of data.

Example 7

Upon discontinuing all medications subsequent to managing the reduction of fasting glucose levels into the normal range, the fasting glucose level rose to about 105 mg/dL and then stabilized illustrating the reversal of T2D with the three month treatment with Orlistat and GLUT2 inhibitor (Canafliglozin or Dapagliflozin).

Example 8

The 56 year old subject with T2D undertook postprandial exercise. No Exercise Sensitizer was administered though the glycemic response had improved due to prior use of the method and orlistat. A week was allowed to allow the body to settle down to the absence of Exercise Sensitizers and SGLT2 inhibitors. Over twenty minutes of postprandial exercise glucose readings were taken every 5 minutes for fifteen minutes. Blood glucose levels dropped from about 175 mg/dL to about 135 mg/dL in five minutes and then stabilized at about 115 at ten and fifteen minutes.

Example 9

The 56 year old subject with T2D was treated with Pioglitazone 15 mg and postprandial exercise but no Exercise Sensitizer or SGLT2 inhibitor. Over twenty minutes of postprandial exercise glucose readings were taken every 5 minutes for fifteen minutes. Blood glucose levels dropped from about 175 mg/dL in steps to about 103 mg/dL at about ten minutes and then leveled off. Thus, pioglitazone seems to act like a weak Exercise Sensitizer at this low dose except that it is absorbed into the body and has a significant risk of hypoglycemia associated with it. However, the data here shows that preferred Exercise Sensitizers perform better and with no risk of hypoglycemia since they are not even absorbed by the body.

Example 10

The 56 year old subject with T2D was treated with Exercise Sensitizer Colestipol (1 gm dose) and postprandial exercise. Over twenty minutes of postprandial exercise glucose readings were taken every 5 minutes for fifteen minutes. Blood glucose levels dropped from about 175 mg/dL in steps to about 94 mg/dL in about fifteen minutes.

Example 11

The 56 year old subject with T2D was treated with Exercise Sensitizer Colestipol (1 gm) before each meal and with 60 mg. of Exercise Sensitizer Orlistat and 100 mg. of Canagliflozin daily. After a low glycemic index breakfast of about 300 to 400 calorie low fat yoghurt base sweetened with sucralose and with sliced almonds, raisins, and fruit, postprandial exercise was undertaken. Over twenty minutes of postprandial exercise on an elliptical trainer at a resistance setting of 6, glucose readings dropped to about 81 to 84 mg/dL.

Example 12

The 56 year old subject with T2D was treated with Exercise Sensitizer colestipol (1 gm) before each meal and with 60 mg. of Exercise Sensitizer Orlistat and 100 mg. of Canagliflozin daily. Colestipol (1 gm) was taken before lunch and breakfast while Orlistate at 60 mg. was taken with 100 mg. Canagliflozin before dinner. Supplemental vitamins and calcium were taken in the morning.

After a low glycemic index breakfast of about 300 calorie low fat yoghurt base sweetened with sucralose and with sliced almonds, raisins and fruit, postprandial exercise was undertaken to evaluate the effect of intensity and duration of the exercise.

A PRO-FORM 14.0 SE Space Saver elliptical machine was used with the ramp set at 25 degrees and exercise undertaken for twenty minutes with rpm maintained at about 60. Resistance was set at 5 on the machine. Blood glucose dropped to the low eighties (81 to 84 mg/dL) in twenty minutes for resistance settings of 5 and 4. Repeating the exercise with progressively lower resistance levels to 3 showed a reduction in blood glucose levels to low eighties (81 mg/dL) in fifteen minutes suggesting rapid stabilization of low glucose levels with limited postprandial exercise.

Example 13

A 56 year old subject with T2D was treated with Exercise Sensitizer Colestipol (1 gm) before each meal and with 60 mg. of Exercise Sensitizer Orlistat and 100 mg. of Canagliflozin daily. Colestipol (1 gm) was taken before lunch and breakfast while Orlistate at 60 mg. was taken with 100 mg. Canagliflozin before dinner. Supplemental vitamins and calcium were taken in the morning.

After a low glycemic index breakfast of about 300 calorie low fat yoghurt base sweetened with sucralose and with sliced almonds, raisins and a banana, postprandial exercise was undertaken to evaluate the effect of intensity and duration of the exercise.

A PRO-FORM 14.0 SE Space Saver elliptical machine was used with the ramp set at 25 degrees and exercise undertaken for twenty minutes with rpm maintained at about 60. Resistance was set at 2. Blood glucose dropped to 90 mg/dL in twenty minutes (to 103 mg/dL in 10 minutes and 97 mg/dL in 15 minutes).

This Example shows that even a low resistance setting of 2 suffices to help bring about reductions in glucose levels when assisted by Exercise Sensitizers. Such rapid drop in blood glucose levels without inviting hypoglycemia shows that this approach is far safer for productively combining exercise with medications than has been the case with Traditional Medications.

Example 14

Exercise intensity was estimated by way of blood pressure and heart rate measurements using a portable Relicon wrist cuff monitor. The conditions for exercising were as in Example 13 on the PRO-FORM 14.0 SE Space Saver elliptical machine with the ramp set at 25 degrees and exercise undertaken for twenty minutes with rpm maintained at about 60. Resistance was set at 2. Readings were taken at five minute intervals. The procedure by CDC for measurements is to stop the exercise while measuring the heart rate. That rate was measured at 96 bpm within 30 seconds of pausing. The readings are as in the Table.

The Recommended Highest Heart Rate=208−0.7*58=167 or even 220−age=162.

At 96 bpm, the measurement taken using the CDC regime of pausing (for no more than a few seconds needed to make the measurement) while measuring the heart rate the regime corresponds to 96/167=57% or 96/162=59%. Both are well below the cutoff of 70% to be considered high intensity exercise.

Another way of calculating exercise intensity uses the Recommended Highest Heart Rate-Resting Heart Rate to get a reserve heart rate. In this measure, the Recommended Highest Heart Rate of 167 leads to a reserve of 108 and the Recommended Highest Heart Rate of 162 corresponds to a reserve of 103. Then (96−59)/108=34% and (96−59)/103=36% of the heart rate reserve being used by exercise. It should be noted that this intensity of exercise is far below what is recommended for managing T2D by reducing weight.

All numbers are rounded or truncated.

|  | Systolic | Diastolic | Heart Rate | Notes |
| --- | --- | --- | --- | --- |
| Resting Prone | 107 | 65 | 59 |  |
| 5 minutes | 124 | 70 | 84 | While pedaling |
| 10 minutes | 134 | 76 | 117 | While pedaling |
| 15 minutes | 114 | 67 | 96 | Paused pedaling CDC procedure |
| 20 minutes | 135 | 81 | 119 | While pedaling |

Example 15

Exercise intensity was estimated by way of blood pressure and heart rate measurements using a portable Relicon wrist cuff monitor. The conditions for exercising were as in Example 11 on the PRO-FORM 14.0 SE Space Saver elliptical machine with the ramp set at 25 degrees and exercise undertaken for twenty minutes with rpm maintained at about 60. Resistance was set at 6. Readings were taken at five minute intervals. The procedure by CDC for measurements is to stop the exercise while measuring the heart rate. The heart rates measured were at about 96 bpm within 30 seconds of pausing. The readings are as in the Table below.

|  | Systolic | Diastolic | Heart Rate | Notes |
| --- | --- | --- | --- | --- |
| Resting Prone | 110 | 67 | 59 |  |
| 5 minutes | 118 | 65 | 89 | Paused pedaling CDC procedure |
| 10 minutes | 106 | 67 | 96 | Paused pedaling CDC procedure |
| 15 minutes | 110 | 60 | 96 | Paused pedaling CDC procedure |
| 20 minutes | 106 | 58 | 100 | Paused pedaling CDC procedure |

The heart rate of about 95 (average of those at 5 min., 10 min., 15 min., and 20 min. time points) achieved in this regime corresponds to 95/167=57% of the Recommended Highest Heart Rate. Using the older formula the numbers work out to be 95/162=58%. Both are well within the 50% to 70% range for moderate intensity exercise. All numbers are rounded or truncated.

Example 16

A 57 year old subject with T2D was treated with Exercise Sensitizer Welchol (625 mg) in the morning and evening before breakfast and dinner respectively. Supplemental vitamins and calcium were taken in the morning. Fasting blood glucose level was 102 mg/dL. After a about 400 to 500 calorie breakfast of yoghurt sweetened with sucralose accompanied with a handful of almonds and peanuts with some rice flakes, postprandial exercise was undertaken to evaluate the effect of intensity and duration of the exercise. The conditions for exercising were as in Example 11 on the PRO-FORM 14.0 SE Space Saver elliptical machine with the ramp set at 25 degrees with rpm maintained at about 60. Resistance was set at 6. Readings were taken at ten minutes, next five minutes, next five minutes, next ten minutes, next ten minutes, next ten minutes, next ten minutes and another ten minutes time points. The readings blood glucose at each of the resulting time points of 0 minutes, 10 minutes, 15 minutes, 20 minutes, 30 minutes, 40 minutes, 50 minutes, 60 minutes and 1 hour, 10 minutes were found to be 124 mg/dL, 98 mg/dL, 102 mg/dL, 98 mg/dL, 95 mg/dL, 96 mg/dL, 84 mg/dL, 100 mg/dL, and 97 mg/dL respectively. The 84 mg/dL was confirmed with a fresh strip from another batch within seconds and found to be 88 mg/dL, which suggests that it indicates a minimum after which gluconeogenesis resulted in an increase in blood glucose levels.

After cessation of exercise on the elliptical machine of about 1 hour, 10 minutes, blood glucose was tracked about every hour to estimate the time course of change in blood glucose levels between meals. At about two hours and ten minutes after starting the exercise (about one hour after ending the exercise), blood glucose level was determined to be 115 mg/dL with about 16 oz. of diet Pepsi being ingested. At about three hours and ten minutes after starting the exercise (about two hours after ending the exercise), blood glucose level had reduced back to 100 mg/dL without requiring exercise, suggesting that the diet soda resulted in some limited gluconeogenesis, possibly due to stimulants like caffeine in it or due to other ingredients. At four hours and thirty minutes after starting the exercise (about three hours and thirty minutes after ending the exercise), blood glucose level was determined to be 98 mg/dL.

Compatibility with Weight Management and HbA1c Reduction

Further treatment would likely reduce HbA1c numbers further as the post meals glucose levels are reduced and compliance improves. Notwithstanding the long list of failures in treating T2D, aspects like smartphone implementations are being explored. Several companies have independently taken up the task of creating noninvasive detection of glucose. Google has been disclosed efforts in developing a contact lens with blood glucose measuring capabilities. Even if an effort at developing a contact lens succeeds, the device would have the same challenge as current manufacturers of portable home glucose meters and strips, viz., there is no use for the devices in the largest group of diabetics—the T2D patients and prediabetics. This is because other than flag hypoglycemia, the glucose strip does not guide treatment decisions.

In our methods outlined here, it is possible to instruct a physician or a patient to use a Postprandial Feedback Meter in the postprandial state to track the reduction in glucose levels—such as was done for Examples 12 and 13. A noninvasive Postprandial Feedback Meter would be even better since it would entirely take away the discomfort of a prick to draw blood. Quick LLC is developing one such meter based on saliva while GlucoTrack is made by an Israeli company that uses Ultrasound, Electromagnetic and other radiations to track glucose in a meter that requires fewer consumables. Sanofi also has a strip that can detect glucose in the skin and communicate the values wirelessly—in the manner envisaged by sensors built into lenses and saliva based testing. All of these devices would benefit from our method and vice versa since they will make it possible for a user to not only evaluate their meal size—this approach is better than the 'soda tax' or ban being experimented with—but also engage in enough exercise to avoid the harm flowing from high blood glucose levels.

Exemplary Embodiments

Described next are more practical exemplary glucose measuring devices for the postprandial context to facilitate the implementation of our method. It is noteworthy that presently the utility of portable glucose meters is in question and their use is falling since they fail to deliver a clear medical benefit. As is seen from the example above and the following description and discussion, appropriately designed Postprandial Feedback Meters and consumables are sorely needed for reversing or arresting the progression of T2D. Such exemplary glucose measuring devices for postprandial use have the capability for both invasive and noninvasive glucose detection.

Exemplary Glucose Measuring Device

Our preferred exemplary Postprandial Feedback Meter uses a bodily fluid like saliva to noninvasively monitor glucose levels while it also includes the ability of using blood/plasma for getting more accurate results as well as calibrating the noninvasive testing against the more accurate values obtained using invasive glucose detection. Alternatively, it is possible to use spectrometric methods to estimate glucose levels in saliva or even through the skin. It should be noted that similar results may be obtained using conventional invasive glucose testing devices. If using electrochemistry then the reactions for saliva are similar to that with whole blood or plasma samples in that glucose oxidase is used to generate Hydrogen Peroxide:

$$\text{glucose} + \text{GOx}(ox) \rightarrow \text{gluconic acid} + \text{GOx}(red) \tag{1}$$

$$\text{GOx}(red) + 2M(ox) \rightarrow \text{GOx}(ox) + 2M(red) + 2H+ \tag{2}$$

$$2M(red) \rightarrow 2M(ox) + 2e- \tag{3}$$

Here GOx(ox) is glucose oxidase in its oxidized state. GOx(red) refers to the reduced state of the enzyme. M stands for metal (of an electrode) while M(ox) refers to a metal oxide.

Most portable (or home use) glucose meters uses a tiny finger prick to draw about 0.3 ml or even less of blood, which is applied to disposable strips with two or three electrodes or groups of electrodes: (i) the working electrode—which has the glucose oxidase or glucose dehydrogenase enzymes, glucose hexokinase, any required molecules like flavin adenine dinucleotide glucose dehydrogenase with required buffers and cofactors associated with it to generate a glucose sensitive signal; (ii) the counter electrode to complete the circuit with the working electrode and carry most of the current; and (iii) a reference electrode, which is used as a voltage reference and is perturbed as little as possible by ensuring little current is drawn from it. Glucose Oxidase is the preferred enzyme because it is specific for glucose and generates a sensitive signal reflecting the level of glucose with little effect due to the presence of sugars like maltose.

One may need four to six measurements a day—each corresponding to a prick on a finger—which makes the current devices impractical for sustained use. Including noninvasive glucose detection would make such glucose testing practical. While GlucoTrack is expensive upfront it does not require fresh strips for each measurement, combining it with invasive testing is preferable.

For using saliva it is an additional complication that not only is there little glucose in saliva—about one fiftieth of that in blood/plasma, but that glucose is continually absorbed from the oral cavity due to the presence of glucose transporters, including SGLT1 type transporters, as well as the enzyme amylase, which generates glucose—both processes compromise the stability and accuracy of inferring plasma glucose levels from salivary glucose.

A commercially viable purely noninvasive portable glucose measuring device remains impractical since one of the requirements is that each new generation of portable glucose measuring devices be at least as accurate as the preceding ones.

Further, in an aspect, to induce salivation to get fresh saliva samples more representative of plasma/blood glucose, we propose not only rinsing the mouth but to use inhibitors of glucose transporters SGLT1, SGLT2 in a lozenge or another device to induce fresh saliva. Thus, containing lozenge comprising α-methyl-D-Glycoside or Phlorizin, both being inhibitor/substrate of SGLT1 and/or SGLT2, nonsugar and noninterfering sugar substitutes, such as xylitol, to induce saliva and inhibitors of α-amylase, such as maltohexaose and maltododecacose attached to the C-4-OH of acarbose (G6-Aca & G12-Aca) will both prevent generation of glucose in the oral cavity and prevent update of glucose from the oral cavity. A preferred SGLT1/SGLT2 inhibitor is Phlorizin, a compound isolated from nature (a flower for instance) and which started the search for a better compound. Phlorizin has activities against both SGLT1 and SGLT2 but is too unstable to make it past the stomach. Thus, it is desirable to prevent uptake of glucose from saliva to give a stable representation of glucose levels reflecting those in plasma/blood. Further, a mouth rinsing preparation that also includes inhibitors of SGLT1 is useful. Reducing sodium levels would also help reduce SGLT1 activity in the oral cavity. Another alternative is, for instance, Sotagliflozin (an inhibitor of SGLT1 and SGLT2), which may be combined with others like Dapagliflozin, Empagliflozin, or Canagliflozin (each an inhibitor of mostly SGLT2—they are selected to for as little cross activity as possible against SGLT1) provides for further inhibition of glucose uptake from saliva while also promoting excretion of glucose. Such a lozenge and treatment of a subject improves the stability of glucose levels in the saliva and insures that they more closely reflect those in blood/plasma.

Figure 6:
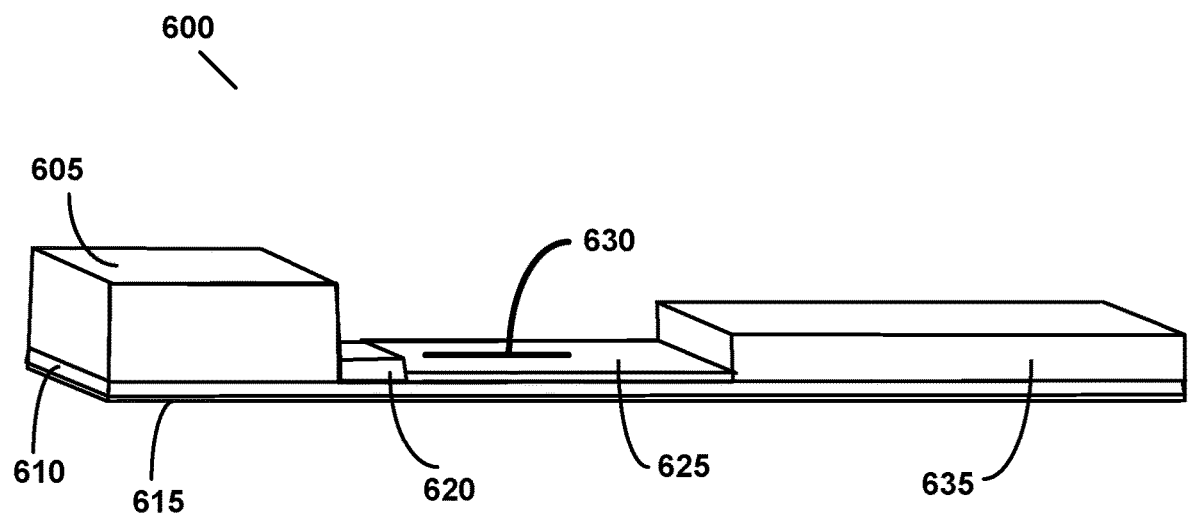
FIG. 6 shows an exemplary consumable for hosting a sensor for detecting glucose/triglycerides/creatine/creatinine.

Thus, a saliva inducer that also spikes saliva with Phlorizin/Sotagliflozin and inhibitors of amylase is desirable to allow for reliable and sensitive glucose detection. Whether such a spike is provided by way of a lozenge, paste—for instance for use in a toothbrush like device described in U.S. Pat. No. 6,623,698, or lyophilized deposits, it is useful to prepare saliva properly. FIG. 6 shows some aspects of a saliva testing consumable 600. Consumable 600 has a receiving trough 605 in which saliva can be spit out. Trough 605 may advantageously include lyophilized deposits of inhibitors of amylase to stabilize saliva. Trough 605 rests on a fluid impermeable bed 610 with a backing 615. Trough 605 is fluidly coupled to a filter 620 to keep out particulates and bubbles. Area 625, coupled to filter 620 allows saliva to flow by sensor 630 using capillary action. Fluidly connected block 635 acts as a sink for the saliva. Preferably block 635 can be replaced if it gets too saturated to pull saliva from trough 605. While the electrical contacts are not shown in this illustration, the electrochemistry is well known. In some embodiments, the electrodes advantageously include sensors for detecting Triglycerides, which is present in amounts reflecting, but at much lower absolute levels, the level in plasma/blood in saliva. To this end, the electrodes have a lipase to break down fats into glycerol and fatty acids. Then, glycerol oxidase generates hydrogen peroxide to provide an estimate of changes in triglyceride levels in saliva. Since hydrogen peroxide is generated, it is also possible to integrate detection of glucose with that of triglycerides on the same working electrode by adding glucose oxidase to provide a signal reflecting the value corresponding to a preceding meal since glucose is also detected by way of generation of hydrogen peroxide. This integration for detecting them in saliva is also possible in an invasive test using blood. In both cases, longer integration periods lead to a better signal.

The current and anticipated regulatory requirements address the risk posed by the failure to detect hypoglycemia and failure to detect extreme hyperglycemia. The rational is that in such situations the clinical decision would likely be affected by the meter results—for instance in a failure to timely ingest glucose. As a result close to the lower end of normal glucose levels, 75 mg/dL 99% of portable meters ought to provide reproducible readings, which means within 15% of the measured value—stricter than the requirement for being within 20% of the measured value. Further, 99% of the meters should satisfy this performance target.

At 75 mg/dL the best portable glucose meters on the market meet the requirement for being within 15% standard at 100%. If the repeated readings should not vary by more than 10%, then the best portable meters perform at 98% to 100%. With even stricter standards of repeated readings not varying by more than 5%, the best meters perform at about 95% to 98% of the tested portable meters or readings but many portable meter brands falter to numbers well below 50%. For the best portable meters the 5% reproducibility standard at about 75 mg/dL glucose levels gives an error of about 3.75 mg/dL or less. In practice the error seems to be of the order of 1 mg/dL or slightly less on the best meters.

In a prospective instrument measuring glucose in saliva, the use of a difference amplifier increases the sensitivity and with the use of catalysts and suitable membranes the electrode is made very specific for glucose by screening out interferrants. Increasing detection times from about 5 seconds to about 2 minutes further improves the resolution of the noninvasive measurements to a fraction of a mg/dL. Combining these with spectrometric detection of glucose in saliva provides a robust mechanism to measure glucose levels.

Figure 4:
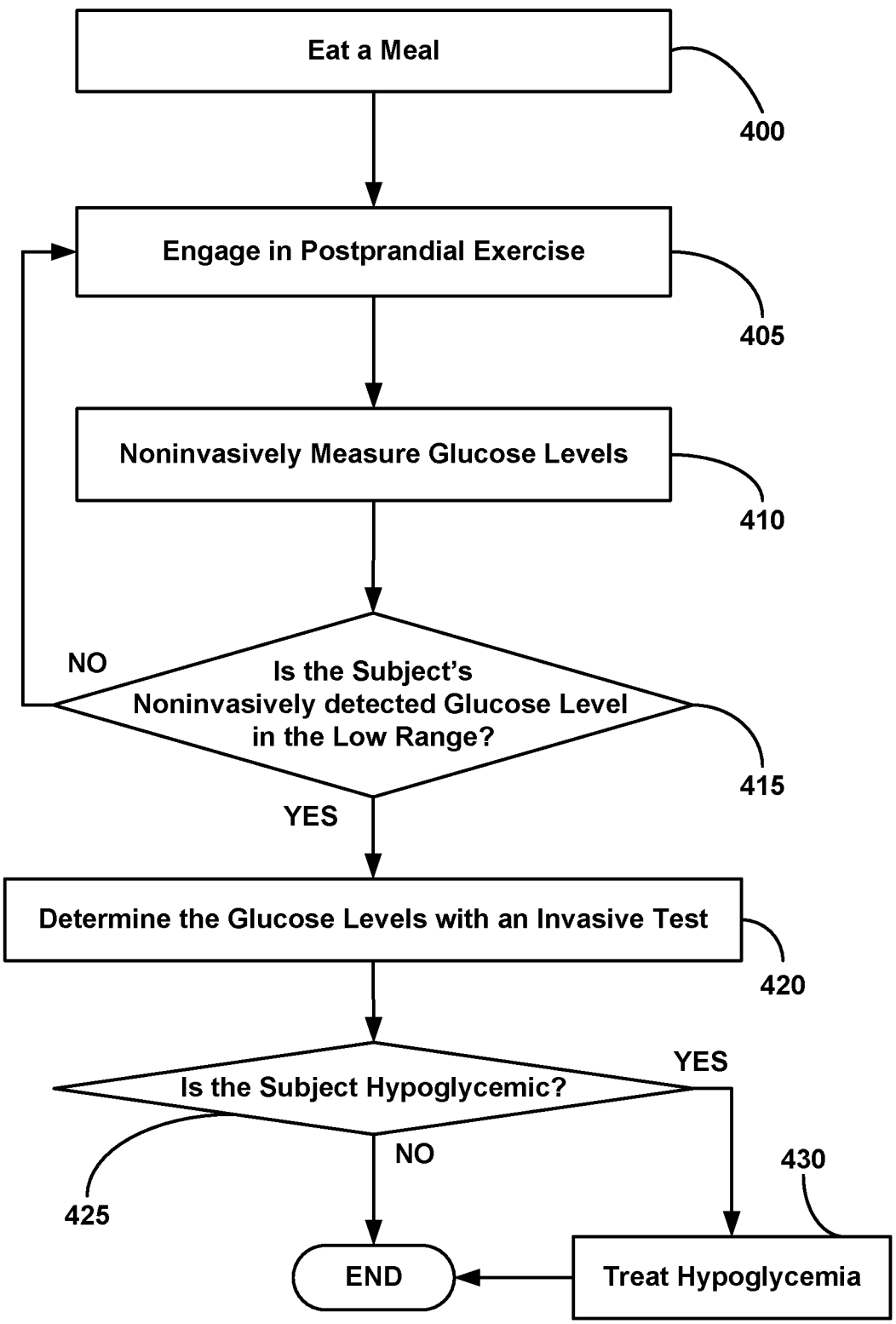
FIG. 4 shows an illustrative method for noninvasive detection of glucose.

In addition to the reproducibility standard, the accuracy of the portable meter—as measured against laboratory measurements varies since it depends on the stability of the calibration. Home use glucose meters encounter more variations in conditions from long term storage of strips to contaminated blood samples or interfering agents in blood, hematocrit, temperature, or even inadvertent dilution due to wet hands. They generally are within 10% for the best portable glucose meters. Best portable glucose meters measure glucose levels accurate to within about 1 mg/dL compared to laboratory analyzers, which is sufficient to meet the need to detect hypoglycemia or hyperglycemia upon retesting with an invasive glucose measurement as is depicted in FIG. 4.

With both invasive and noninvasive capabilities built into the same instrument, as is the case with the Postprandial Feedback Meter difficulties in detecting and flagging hypoglycemia are overcome. This is illustrated in FIG. 4. During step 400 a meal is ingested. Next, during step 405 postprandial exercise is undertaken, during which or better following which in step 410 glucose levels are detected noninvasively. If the glucose level is detected to be in the low' range in step 415, then the meter flags the readings as requiring invasive testing in step 420. Invasive testing can be done on the same instrument using blood/plasma instead of saliva. Control flows from step 420 to 425 for determining if the subject is hypoglycemic. If hypoglycemic, treatment is offered in step 430. Else the routine exits.

Presently the glucose readings are not considered useful if obtained after a meal or during or immediately after exercise because they change rapidly. We have discovered that this is actually the best time period to determine glucose levels in a T2D patient since this is when the defective glycemic response results in persistently high glucose levels in the patient. Lowering them using postprandial exercise and Exercise Sensitizers and SGLT2 inhibitors helps control and reverse the development of T2D.

Figure 5:
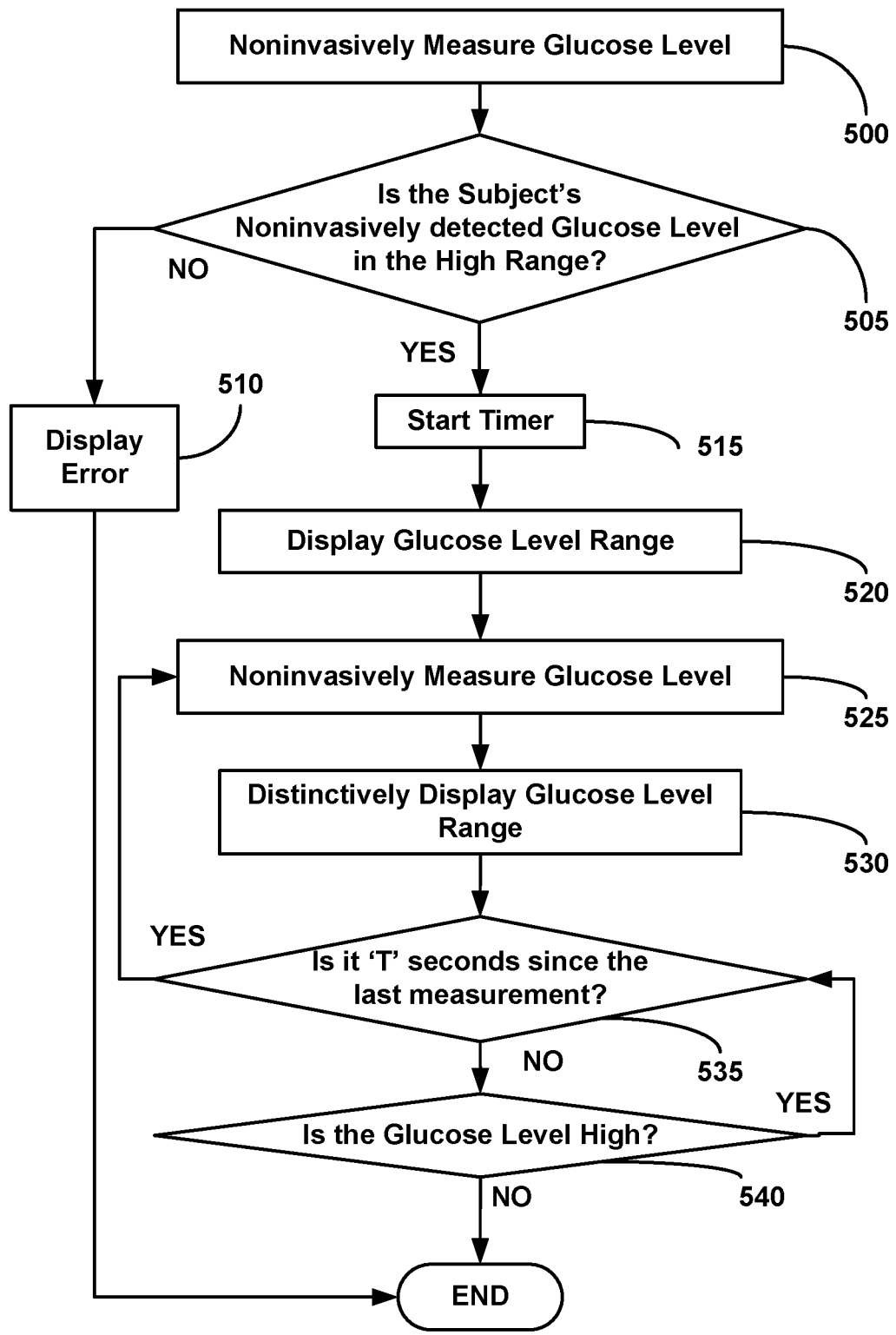
FIG. 5 shows an illustrative noninvasive postprandial glucose level displaying method such that they look different from invasively obtained glucose levels.

In one embodiment of the post-prandial monitoring device both noninvasive and invasive detection of glucose are possible. The Postprandial Feedback Meter indicates invasive glucose detection with greater accuracy than noninvasive glucose detection. Typically this is reported as a concentration in familiar units like mg/dL or mmol/liter. Further the noninvasive detection is readily distinguished from the invasive detection of glucose as the latter is communicated by way of broad categories such as 'low', 'normal', 'high', which makes possible use of noninvasive glucose monitoring using a portable glucose measuring device. This is illustrated in the exemplary embodiment of FIG. 5.

Glucose is measured noninvasively in step 500. In step 505 it is determined if the glucose level is 'High'. If not, control passes to step 510 and an error is flagged because in the absence of high glucose levels it is unlikely that measurements are starting in postprandial state. Else control passes to step 515, during which a timer is started to allow periodic glucose readings. Glucose readings are displayed as a range in step 520 to distinguish them from the more concentration units based readings from standard more accurate invasive testing. In step 525, glucose is measured noninvasively and again the displayed readings are updated in a range based display in step 530. Step 535 allows for testing if a preset time 'T' has passed. If yes, then another noninvasive test is made and control returns to step 525. Else, control flows to step 540, during which is determined if the glucose level is 'high'. If not, the routine exits. Else control flows to step 535 to allow for 'T' time to pass prior to making another measurement.

To minimize the need for invasive glucose detection, e.g., by pricking a finger, an exemplary Postprandial Feedback Meter accepts a disposable noninvasive detection strip with electrodes or an electrode arrangement suitable for analyzing a biological fluid selected from the group consisting of saliva, tears and/or sweat to allow for non-invasive monitoring. Such strips are typically manufactured by depositing the electrodes and connectors on a support with membranes, and, if needed, filters added. In a preferred embodiment a plurality of electrodes is disposed below a membrane such that there is at least one noise measuring electrode for measuring the background and a glucose electrode associated with an enzymatic portion to provide a signal responsive to glucose levels.

Typically when measuring glucose in blood/plasma, the reaction leads to a current when using glucose oxidase, thus making an amperometric detection. A voltage is applied by the meter and the electrode current is read as a measure of glucose. This works well when glucose levels are high and most glucose meters on the market use a similar approach. With low levels of glucose or with very small samples of blood/plasma it is preferable to use background cancellation and other techniques to reduce the background to detect a very small signal. Further, instead of a very quick detection—current portable meters detect glucose levels in about 5 seconds—detection over more time allows integration of more data points and improves sensitivity. As a result, the postprandial noninvasive testing need not detect and report the first glucose levels in 5 seconds but could take one or more of the time periods from the group consisting of about 10 seconds, about 15 seconds, about 20 seconds, about 25 seconds, about 30 seconds, about 35 seconds, about 40 seconds, about 45 seconds, about 50 seconds, about 55 seconds, and about 60 seconds or more but less than about 2 minutes. Preferably it further continues updating the glucose values as fresh sample of noninvasively obtained biological fluid is applied to provide continuous detection.

In a preferred embodiment use is made of the ability to detect creatinine and creatine in saliva using electrochemistry. By way of explanation, detection of creatinine is customary for evaluating kidney function. Creatinine is ordinarily in equilibrium with creatine in the body and elevated creatinine levels indicate kidney malfunction since it is a waste product that is eliminated by the kidney. Healthy folks have creatinine levels at less than about 1 mg/dL although muscular men may have as much as 1.3 mg/dL. Higher levels are flagged as requiring attention. Although other enzyme choices are possible, one set from U.S. Pat. No. 6,861,232 is as follows:

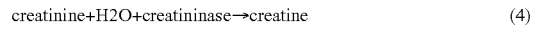

$$\text{creatinine} + H2O + \text{creatininase} \rightarrow \text{creatine} \tag{4}$$

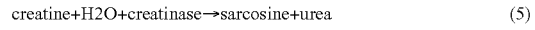

$$\text{creatine} + H2O + \text{creatinase} \rightarrow \text{sarcosine} + \text{urea} \tag{5}$$

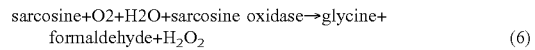

$$\text{sarcosine} + O2 + H2O + \text{sarcosine oxidase} \rightarrow \text{glycine} + \text{formaldehyde} + H_2O_2 \tag{6}$$

Figure 7:
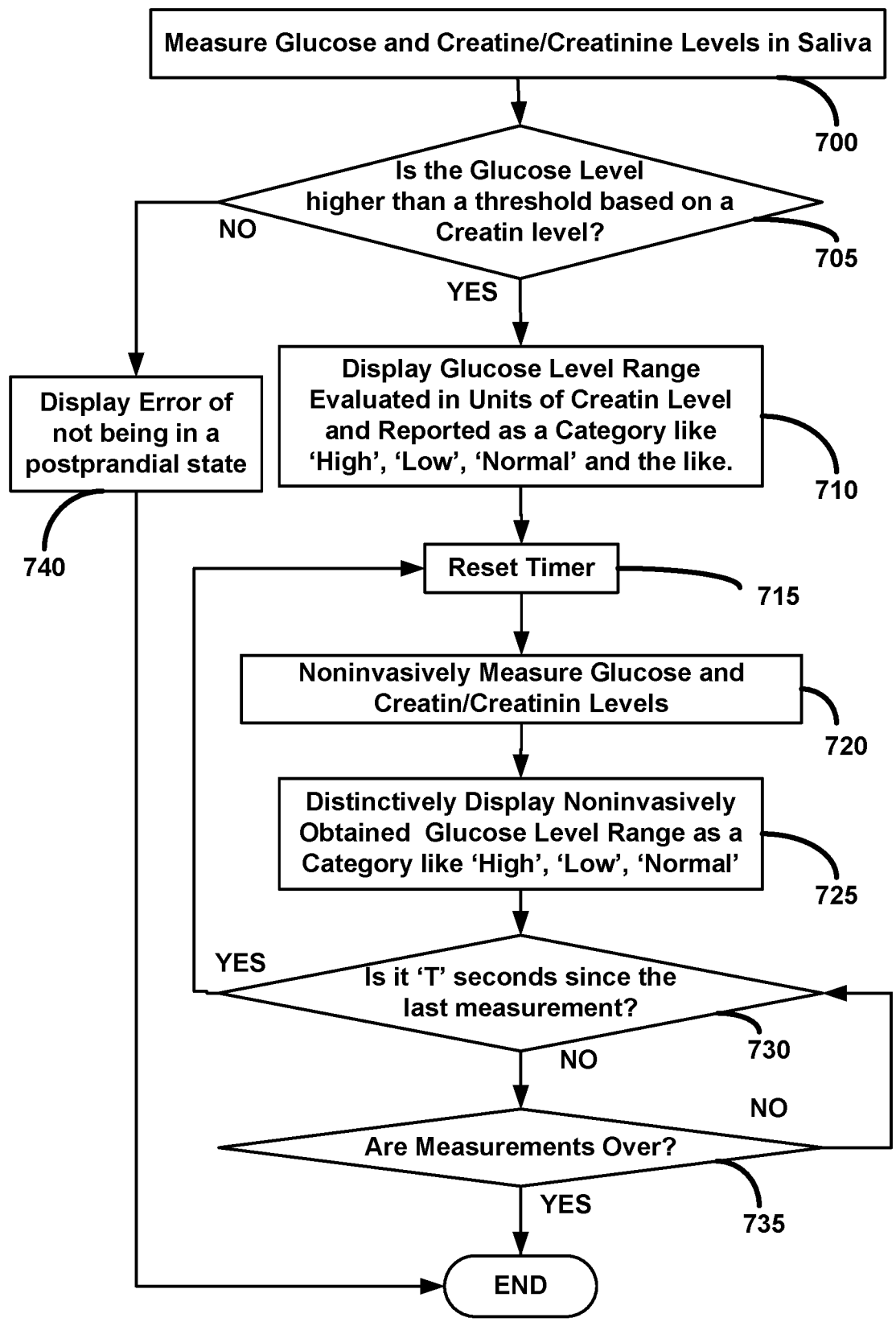
FIG. 7 shows an illustrative method and exemplary postprandial device for measuring glucose, creatine and creatinine levels to use creatine as an internal standard.

As is readily seen in the above equations, the end product detected is $H_2O_2$. Thus, it is possible to detect just creatine using the formulation of equations 5 and 6. Or total level of creatine and creatinine may be detected by adding the enzyme creatinase to further add the signal due to creatinine from equation 4. While creatinine is a waste product and can build up in blood/plasma, creatine is required by muscles and other cells for their functioning. It is made in the liver, kidney and the pancreas and transported to other tissues like muscles via blood. It is taken up from blood using active Sodium driven transporters. The level in blood for creatine rarely goes up since it is taken up aggressively in a manner similar to that of glucose removal from urine and most secreted biological fluids. The level of creatine in blood is relatively steady as it is pumped out until equilibrium is reached at a level of about 20 to 60 micrograms/dL and does not change appreciably over a few minutes of exercise. This is true for creatinine as well. Thus, it becomes to provide an internal standard in saliva, which has about one seventh the level of creatine and creatinine as serum/plasma, using the creatine level at the beginning of a measurement. Then creatinine is also measured in units of initial creatine and so can glucose be measured. With no more than a scaling factor to relate comparable concentrations of creatine and glucose, it is possible to better flag glucose levels at low glucose concentrations—that is after a few minute of exercise when glucose levels would fall. For individuals on Traditional Medications as well as Exercise Sensitizers hypoglycemia remains a concern. The use of creatine levels as an internal standard provides a ready measure for dangerously low glucose levels even in a glucose poor fluid like saliva. FIG. 7 provides an illustration of such a Postprandial Feedback Meter although many variations are possible. It goes without saying that folks taking creatin supplements or with disorders in creatin transporters will not be proper candidates for such a procedure and instrument.

In step 700 both glucose and creatinine and creatin are detected. Then glucose level is checked in step 705 against a threshold derived from the creatin level. These compounds provide a ready measure of plasma derived fluids and of an analyte from plasma that is generally held in a narrow range without being subject to pumps like the SGLT pumps. Glucose ranges are displayed in step 710 unless the glucose levels are not high enough to warrant being in a postprandial state. Control passes to step 715, during which a timer is started to allow periodic glucose/creatine/creatinine readings. Glucose levels, and optionally creatin/creatinine levels, are measured in step 720. In step 725, glucose levels are displayed after updating as a range. Step 730 allows for testing if a preset time 'T' has passed. If yes, then another noninvasive test is made and control returns to step 710 for resetting the timer. Else, control flows to step 735, during which is determined if measurements are complete. If so, the routine exits. Else control flows to step 730 to allow for 'T' time to pass prior to making another measurement.

However, reliability and accuracy of noninvasively detected glucose levels to estimate blood/plasma glucose levels is often insufficient to allow reliably distinguishing between normal (about 70 mg/dL glucose) and hypoglycemia (about 60 mg/dL glucose) since in corresponding noninvasively obtained fluids the resolution has to be good enough to distinguish between 1.4 mg/dL and 1.2 mg/dL, which is beyond the range of current portable glucose meters. Therefore, when glucose levels are low, the Postprandial Feedback Meter is used to detect glucose in blood/plasma to verify the results from noninvasive glucose testing and act to correct hypoglycemia if detected. Further, in the postprandial context it is easier to detect most glucose levels since they are already elevated.

In an embodiment the same exemplary strip can be used to detect glucose invasively or noninvasively. In this embodiment the signal level is dramatically lower when using saliva, tears and/or sweat compared to that in blood/plasma, which can be used to identify if the biological fluid is blood/plasma or sweat/tears/saliva. The Postprandial Feedback Meter detects may automatically decide that the biological fluid is blood/plasma or one of sweat, tears or saliva. Further, the user can confirm the determination by the device or the absence of hemoglobin can be used to confirm the absence of blood/plasma on the strip when low levels of glucose are detected.

The Postprandial Feedback Meter has an electrically conductive slot to receive a disposable invasive/noninvasive strip for analyzing blood or plasma. It decides if the fluid is blood/plasma by one or more of (i) recognizing the range of the difference signal for blood being many fold greater than from tears, sweat, or saliva, (for instance a glucose level of about or less than 20 mg/dL (at levels of 50 mg/dL a person is cognitively impaired) is presumed to be noninvasively obtained while a noninvasive detection of about 6 mg/dL corresponds to about 200 mg/dL level in blood/plasma) or, alternatively, (ii) recognizing the disposable invasive/noninvasive strip as being suitable for analyzing blood by its shape or an indicator included in the disposable invasive/noninvasive strip. This indicator may be the presence hemoglobin or any other blood component level. Then both the absence of hemoglobin and the lower signal level would indicate noninvasive monitoring.

Hypoglycemia Detection in Noninvasive Glucose Detection

One of the major concerns in using glucose meters is the risk of a failure to timely detect hypoglycemia. Erroneous indication of hyperglycemia or hypoglycemia or a failure to accurately detect hypoglycemia and the like are all reasons for a glucose meter to be found unacceptable. At the lower end, normal glucose levels in plasma are at about 70 mg/dL and 60 mg/dL for hypoglycemia with 50 mg/dL indicating severe hypoglycemia, which at one fiftieth of this blood/plasma concentration are noninvasively detected in saliva as 1.4 mg/dL, 1.2 mg/dL, and 1 mg/dL respectively. At a detection limit of 0.5 mg/dL it is possible to distinguish between 1.3 mg/dL and 1.8 mg/dL. Thus, in saliva a glucose level of about 1.8 mg/dL is in the normal range while 2.3 mg/dL is near the upper end of the normal range while at or above about 2.8 mg/dL is hyperglycemia. The closer the glucose levels get to about 1.3 mg/dL in saliva, the greater the possibility of missed hypoglycemia. The latter possibility is addressed in our method by follow up invasive testing to ensure the actual blood/plasma level is not too low compared to about 70 mg/dL, the lower limit for normal glucose levels. Thus, noninvasive testing for glucose possible with a Postprandial Feedback Meter device to help determine if postprandial exercise is adequate without a significant risk of missing hypoglycemia in rare instances. It should be noted that the risk of hypoglycemia is low in the postprandial time period anyway and the risk is even lower if Traditional Medications are not used as was the case in the described illustrative examples. Thus, an acceptable glucose meter has to distinguish between glucose at about 70 mg/dL and 60 mg/dL and not fail to detect glucose at 50 mg/dL or lower. The exemplary Postprandial Feedback Meter meets this requirement because current invasive blood/plasma analyzing devices already satisfy this requirement.

In the exemplary description above, a noninvasive glucose detection device with a limit of 1 mg/dL can detect normal ranges at levels of about 2.3 mg/dL as in saliva as postprandial glucose levels fall to this level with exercise. If the levels fall below about 2 mg/dL, follow up noninvasive testing may be used to ensure the absence of hypoglycemia. By using creatine levels as an internal standard allows another measure to flag possible hypoglycemia even early and reliably.

The use of a glucose detection device having both invasive and noninvasive detection allows invasive detection of glucose levels when the noninvasive detection indicates even the possibility of hypoglycemia to allow timely intervention. Further the use of categories for noninvasive glucose level reporting readily allows recognition of noninvasive readings from invasively obtained glucose levels when used in a post-prandial setting, as is the case for a Postprandial Feedback Meter, the risk of encountering hypoglycemia is remote since the subjects have just been subjected to a glucose level spike due to the preceding meal.

The Postprandial Feedback Meter has a display that indicates sufficiency of exercise for glycemic control if it detects glucose level falling below a threshold, or a reduction by a prescribed percent of a peak blood glucose level, or being within a prescribed range for the blood or plasma glucose level, or the blood/plasma glucose level being less than about 110 mg/dL, more preferably being less than about 100 mg/dL, and most more preferably being less than about 90 mg/dL.

Such a drop tells the user that the post-prandial exercise can be stopped although there is no requirement to cease exercising immediately. In one embodiment, the Postprandial Feedback Meter display indicates the glucose level as one of the group consisting of 'Low', 'Desired', 'Moderately High', 'Excellent', and 'Too High' categories, wherein for blood/plasma the low' category encompasses a range of below about 75 mg/dL, the 'Desired' category encompasses a range from about 70 mg/dL to about 130 mg/dL, more preferably from about 70 mg/dL to about 120 mg/dL, and most preferably from about 70 mg/dL to about 100 mg/dL, the 'Moderately High' category encompasses a range from about 130 mg/dL to about 180 mg/dL, the 'Excellent' category encompasses glucose levels of about 70 mg/dL to about 80 mg/dL and the 'Too High' category corresponds to glucose levels of about 180 mg/dL or higher. Corresponding categories for noninvasive glucose detection can be specified taking into account the limit of glucose detection. In an aspect, some of the categories may overlap and even multiple categories may be displayed to a user to provide a sense of changes in glucose levels as they go down with postprandial execise.

Alternative categories may be implemented to reflect the limitations in estimating blood/plasma glucose levels from those detected noninvasively. Thus, in view of the lower glucose levels in such fluids, only three categories could be implemented, such as 'Low', 'Acceptable' and 'High', with the low' category reading requiring invasive retesting to address the possibility of hypoglycemia.

In another aspect, an exemplary Postprandial Feedback Meter includes an antenna for communicating over a wireless connection to a smartphone or a smartphone affiliated device or a health or fitness device.

The Postprandial Feedback Meter admits of some novel exemplary consumables. In particular, there is the strip that can be used to measure glucose in blood/plasma as well as saliva/sweat/tears etc. In addition, a lozenge compatible with the strip is preferably used to cause salivation while also inhibiting salivary amylase and SGLT1. This enables reliable detection of glucose levels in the saliva when measuring glucose levels.

Exemplary Compositions

While some patients may not need the Exercise Sensitizer, its use ensures predictable glucose level reductions in response to post-meal/postprandial exercise. With the use of an Exercise Sensitizer the size of the meal need not be impractically small. We determined Orlistat, a pancreatic lipase inhibitor, which inhibits the absorption of fats in the gut among its other effects, as a particularly effective Exercise Sensitizer at even low doses. A low dose of Orlistat makes a subject sensitive to exercise induced blood glucose level reduction after a meal although by itself Orlistat is ineffective in changing glucose levels and may even result in an increase in glucose levels when exercise is undertaken in a fasting state even after ingesting Orlistat. Advantageously Orlistat is not absorbed by the body and is excreted out. Thus, most of its direct effect is on the molecules in the digestive track. It further reduces or even eliminates spikes in blood triglyceride levels after a meal.

The size and nature of the meal is forgiving if together with Orlistat is administered a glucose transporter inhibitor. We used inhibitors of GLUT2, which also help reduce the spikes in glucose levels by helping excrete excess glucose in urine as it is absorbed into the blood/plasma compartment. Further glucose excretion is aided by using better formulated beverages to facilitate excretion of excess glucose without getting electrolytes out of balance. Better design of furniture and fixtures for aiding in such exercise allows the patient to exercise until the blood glucose levels have reached the desired range.

In another aspect, we have discovered that some compositions are useful for making T2D patients' glucose levels more exercise sensitive. Thus, sensitized, a short spell of moderate exercise is sufficient to lower blood glucose levels in as little as five or ten minutes. Combining such sensitization with a glucose excretagogue allows for a very tolerable lifestyle modification routine that does not require tiny meals, unforgiving compliance, or uncomfortably strict dietary controls. An example Exercise Sensitizer composition for controlling blood glucose comprises an effective amount of a lipase inhibitor; an effective amount of a glucose excretagogue to stimulate excretion of blood glucose to reduce the level of blood glucose level; supplemental nutrients and pharmaceutically acceptable vehicles or excipients. Several examples of each of these types of substances are well-known, Thus, for instance in an exemplary composition tetrahydrolipstatin is combined with a glucose excretagogue selected from the group consisting of Canagliflozin ((2S, 3R,4R,5S,6R)-2-{3-[5-[4-Fluoro-phenyl)-thiophen-2-ylm-ethyl]-4-methyl-phenyl}-6-hydroxymethyl-tetrahydro-pyran-3,4,5-triol), Dapagliflozin ((2S,3R,4R,5S,6R)-2-[4-chloro-3-(4-ethoxybenzyl)phenyl]-6-(hydroxymethyl) tetrahydro-2H-pyran-3,4,5-triol), Empagliflozin ((2S,3R, 4R,5S,6R)-2-[4-chloro-3-[[4-[(3 S)-oxolan-3-yl]oxyphenyl] methyl]phenyl]-6-(hydroxymethyl)oxane-3,4,5-triol), Remogliflozin (5-methyl-4-[4-(1-methylethoxy)benzyl]-1-(1-methylethyl)-1H-pyrazol-3-yl 6-O-(ethoxycarbonyl)-β-D-glucopyranoside), Sergliflozin (2-(4-methoxybenzyl)phenyl 6-O-(ethoxycarbonyl)-β-D-glucopyranoside), and Tofogliflozin ((1S,3'R,4'S,5'S,6'R)-6-(4-Ethylbenzyl)-6'-(hydroxymethyl)-3',4',5',6'-tetrahydro-3H-spiro[2-benzo-furan-1,2'-pyran]-3',4',5'-triol hydrate (1:1)), and Sotagliflozin (an inhibitor of both SGLT1 and SGLT2 Sodium Glucose Transport protein types 1 and 2) or a pharmaceutically acceptable salt, hydrate, polymorph, solvate, prodrug, enantiomer, or stereoisomer thereof. A preferred composition includes as a glucose excretagogue Dapagliflozin, Sotagliflozin, Empagliflozin, or Canagliflozin. A more preferred excretagogue is Canagliflozin. An even more preferred excretagogue is Sotagliflozin since it potentially improves glucose detection using saliva by inhibiting SGLT1. Other components preferably included in the exemplary compositions include cholestyramine and colestipol and supplemental nutrients, which inclusion improves the efficacy of the composition.

Of these exemplary compositions we have tested combinations of 60 mg of Orlistat with either 5 mg of Dapagliflozin or 100 mg of Canagliflozin. We have also tested a combination of Colestipol with Orlistat and an SGLT2 inhibitor. Although both combinations performed well, the combination of Colestipol with supplemental nutrients in the morning and the combination of Orlistat and the SGLT2 inhibitor at dinner time are preferable. This routine could be implemented with a blister pack with morning and evening pills that make the task almost error free.

The advantage of the exemplary compositions is that in the trials corresponding compositions sped up the process of recovery from T2D. The Exerciser Sensitizers are not absorbed by the digestive system. Indeed, adding a bile salt sequestrant selected from the group consisting of cholestyramine, colestipol, colestimide, colesevelam, sevelamer, DEAE-cellulose, β-cyclodextrin, γ-cyclodextrin, guanidinoethylcellulose, and DEAE-Sephadex, with Colestipol the preferred tested component, to the composition improves the performance and ease of use with minimal risk of hypoglycemia. In this strategy fine control over glucose levels is by way of exercise and under control of the user. Preferred bile acid sequestrants are cholestyramine and colestipol.

The major benefit provided by the preferred compositions is that they leave the normal gluconeogenesis mechanism unmolested, thus drastically reducing the risk of hypoglycemia while delivering regression of T2D. However, this benefit is reduced if it is necessary to use additional medications in patients with more difficult to treat T2D. Such medications (such as insulin secretegogues like sulfonylureas, insulin sensitizers and gluconeogenesis inhibitors like metformin and the like) likely would be needed at lower doses in most instances, which would further reduce the risk of hypoglycemia but not to the extent possible in the absence of such additional medications. These lower doses for each of the medications have not been determined yet but can be readily determined with routine experimentation.

Weight Loss

A frequent desirable result is weight loss—which is distinct from improved glycemic response and regulation. However, weight loss often is sufficient for improving glycemic response even if it is not always necessary—although it is a far more difficult a target than improving glycemic response. In subjects also desiring weight loss, it is a simple matter to extend on or more of the postprandial exercises to further weight loss. The biggest factor for bringing about weight loss is diet. This our system already modulates using the Postprandial Feedback Meter to control portion size. This disclosure is primarily concerned with improving the glycemic response but is also useful in addressing the related problem of weight loss.

Our Method Bringing Together Exercise Senzitizers and Habits for LifeStyle Changes A treatment for a potentially chronic condition or one requiring treatment over a long period needs to be habit forming in order to be effective. To form a habit one needs at least a cue, a habit routine executed upon detecting the cue and a result—which should be desirable enough to pin down the habit and generate a craving to execute the habit upon encountering the cue—best done more of less subconsciously. Thus, the failure to execute a habit should nag at the subject. Further, FIG. 8 outlines the Habit Lop 800 that can bring about lifestyle changes using our methods. There is Habit Cue 805, which in our methods is implemented preferably as the act of eating or observing the noninvasively obtained glucose level getting higher. Habit Cue 805 causes execution of the Habit Routine 805, which, in turn, results in showing a drop in glucose levels to normal ranges which acts as the Habit Result/Reward 815. After obtaining the Habit Result/Reward the system is primed to sense the next Habit Cue 805 and repeat the Habit Loop 800.

An example of successful habit formation is provided by the adoption of toothpaste for improving dental hygiene by way of regular brushing. Early toothpastes were about equally effective as to dental hygiene and made similar claims. But regular brushing refused to take off. However, one brand suddenly changed this static state of affairs. PEPSODENT™ marketed a toothpaste that promised an alluring smile—as did many others—but also provided a minty aftertaste as a result. The absence of the minty result caused its users to remember to brush and the minty taste told them that brushing was done—it provided a stand-in for the desired result of improved dental hygiene. Similarly, to help folks climb out of a debt trap, 'Pay and Win', an experimental program offered by Lutheran Social Services in Duluth, Minn., offered a raffle drawing to folks overwhelmed by the debt and struggling to make even the minimum monthly payments. Those who steadily paid down their loans each month became eligible for the raffle drawings each month. "When you know you have a hope of winning," says one of the participants, Mrs. Hanson, "what a motivation!" The impetus of a cue in the form of the need to enter the raffle (at no additional cost) to avoid the opportunity cost helped borrowers get their finances in order as well as feel less overwhelmed immediately, which provided a desired result for financial planning. Upon winning the raffle, the learned healthier financial habit encouraged them to pay down the debt to further along the process of self-discipline for better financial management. In treating T2D, lifestyle changes have not happened because the cues and the results are far too distant from the desired behavior and the competing cues for initiating alternative incompatible habits have immediate results in the form of enticing food or simply resting. Thus, providing suitable cues and results for controlling T2D remains an unmet need.

Figure 9:
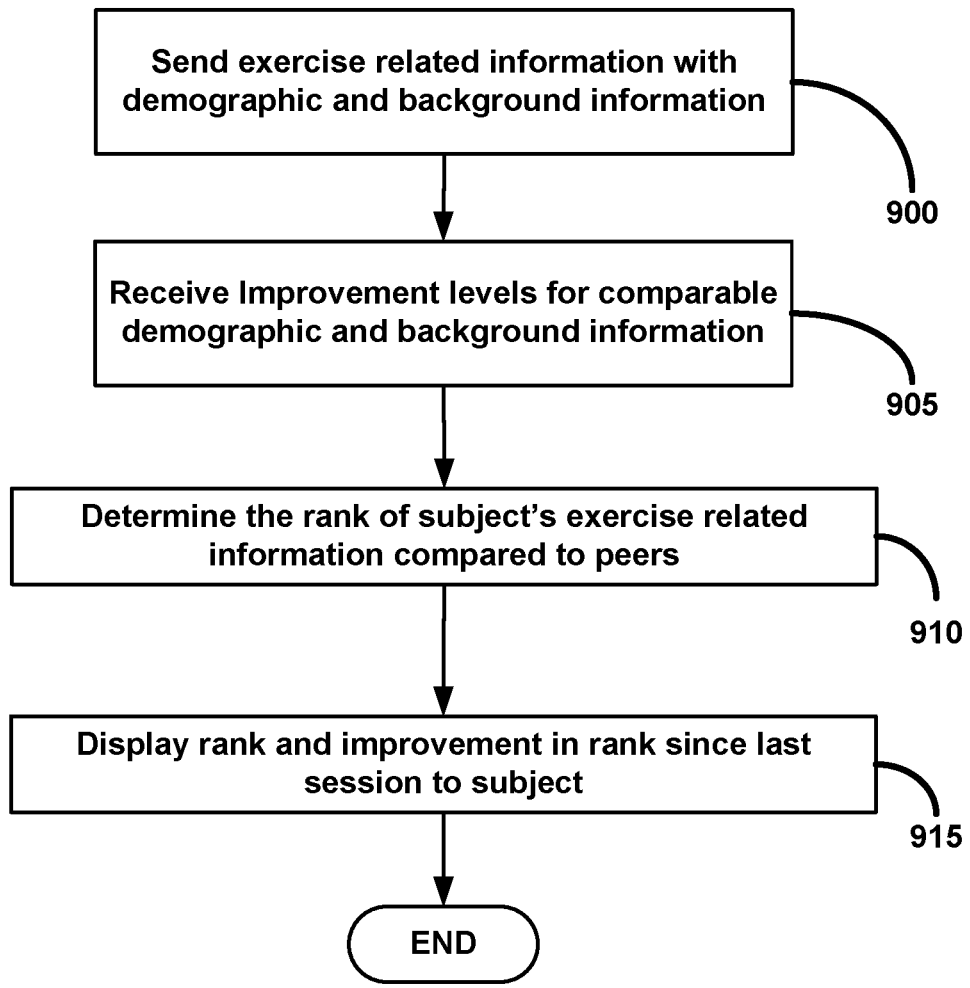
FIG. 9 shows a method for reporting results and motivational statistics to a user to establish desirable habits using a smartphone, smartphone related accessories and health monitoring technology.

We determined that it is possible for many T2D patients, and in particular newly diagnosed or those at risk of developing T2D, to take charge of their blood glucose levels safely and even reverse the disease course by providing rapid feedback on the result of their actions. This feedback is in the form of postprandial glucose levels that provides information on the effect of diet and/or exercise immediately following a meal. FIG. 9 illustrates on such method using the smartphone platform. In step 900 anonymized information is sent to a central server. During step 905 a comparable standards are received. Using the received standards, a rank is calculated for the subject during step 910. Then to promote habits based on performance in a shared community, a rank and improvement is displayed in step 915.

We discovered that exercising prior to a first meal/breakfast is mostly ineffective in substantially changing blood glucose levels in T2D patients although it may be effective for losing weight or building muscle tone etc. As a result mere exercise does not provide immediate feedback or benefit since weight loss is over months, if at all, and a T2D patient can notice few motivating changes flowing from exercising, which is harder due to insulin resistance.

Exercising after a meal, preferably about thirty minutes after a meal is effective in reducing blood glucose levels and reduces blood glucose levels into the normal range with an Exercise Sensitizer making a patient's plasma/blood glucose levels responsive to Post Prandial Exercise ("PPE").

An occasional failure for a rapid reduction in blood glucose levels following post prandial moderate exercise is due to excessive calorie intake. Thus, practicing the method with a small meal is sufficient to demonstrate the efficacy of the method to a patient. Then adjusting the size of the meal is something the patient can do to make sure postprandial glucose levels can be reduced into the desired range.

Figure 10:
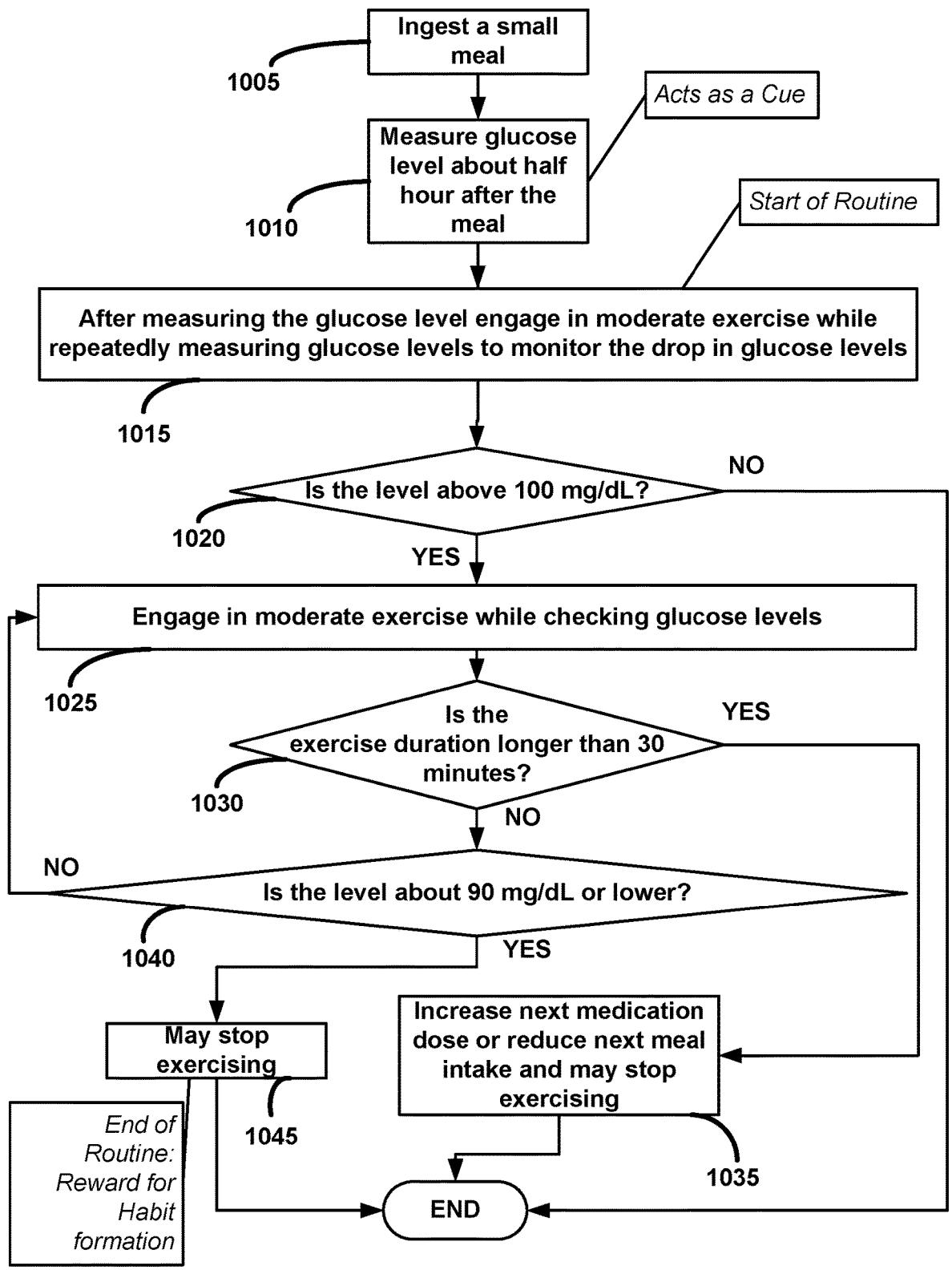
FIG. 10 shows an illustrative method to inculcate habits to treat type 2 diabetes in accordance with our methods.

Most easily digested carbohydrates are absorbed early. Without intending to be bound by theory, we believe that a failure to reduce blood glucose levels to a 'normal' range in about twenty to thirty minutes of exercise indicates excessive caloric intake. As a result, getting a measure of the triglyceride levels is also useful to provide feedback to a subject about the quality and nature of the meal together with the result of glucose level reduction by post-prandial exercise. Over time, by modifying lifestyle with post-prandial exercise and better designed meals the glycemic response improves and allows a subject to transition from being classified as a T2D to being glucose intolerant and even free of T2D. Such a routine is illustrated in FIG. 10.

The desired habit is of regular postprandial exercise to reduce blood glucose levels to the normal range—even if it does not result in weight loss. The disclosed methods generate cues and desirable results using glucose level measurements to indicate sufficient exercise and/or desirable portion sizes. In a preferred embodiment, glucose levels are detected after a meal and lowered using moderate exercise into a desirable range. Such a range may be prescribed by a physician. Thus, the cue is partaking of a meal with concomitant increase in glucose levels. In response to detecting the increase in glucose levels the steps to be executed include postprandial exercise. The reward or results is by way of getting control over blood glucose levels by driving them into a desirable range. The exercise is continued until the glucose levels reach the desired range or exercise has been undertaken for a prescribed duration if the glucose levels do not reach the desired range. Thus Postprandial Feedback Meter operates well in the very zone disfavored by experts for interpreting glucose levels for improving glycemic control and minimizing postprandial glucose spikes. Over time the glycemic response improves and medications are titrated down as T2D reverses.

In an aspect, providing additional sinks for the excess glucose in the blood/plasma compartment further reduces the post meal spike in blood glucose levels by way of glucose excretagogues. The compositions described herein include an Exercise Sensitizer agent, the preferred Exercise Sensitizer agent being tetrahydrolipstatin (Orlistat), a waxy solid. This agent also reduces the postprandial triglyceride spikes and where intense exercise may be needed, using it (or another Exercise Sensitizer) allows for its substitution by a brisk walk.

Our method for improving glycemic control sticks because it is designed to establish habits. Habits are what humans exist by. Psychologists note that habits account for forty percent (40%) or possibly much more of the daily decisions. Once a habit is formed, it is effortless to execute and a failure to execute it nags instead. Here the failure to exercise nags once it is clear that it is within the patient's control to normalize the glucose levels. On the other hand, success in reducing glucose levels provides a sense of control.

In FIG. 10, during step 1005 a small meal is taken. The measurement of glucose levels in step 1010 acts as a Habit Cue resulting in the Habit Routine of moderate postprandial exercise in step 1015. If the glucose level is higher than 100 mg/dL during step 1020, exercise is continued during step 1025. If the exercise duration has been longer than, say thirty minutes, as determined in step 1030, control flows to step 1035 during which either the meal size or the Traditional Medication dose or both are adjusted. Else if the glucose level is determined to be less than about 90 mg/dL in step 1040, exercise can be terminated with a sense of achievement of the Habit Reward/Result of controlling blood glucose levels successfully. If the level is not at or below about 90 mg/dL, Exploiting the Hysteresis in Blood Glucose Levels We discovered that upon reducing blood glucose levels using exercise, the blood/plasma glucose levels increased rather slowly after exercise or even stayed steady. On the other hand, if blood/plasma glucose levels were increased in T2D patient, they decayed slowly. Thus, the rapid reduction in blood/plasma glucose levels brings out a rapid reduction in HbA1c measures.

Synergy Between Post-Prandial Exercise and Medications

We discovered that medications like orlistat synergize with postprandial exercise unlike Traditional Medications that require close supervision in view of heightened risk of harm. Blood glucose levels drop sharply with exercise in an Exercise Sensitizer treated subject. Failure to engage in exercise results in minimal glycemic benefit while exercise without eating after taking orlistat also had minimal effects.

Providing for Non-Invasive Monitoring

Invasive glucose monitoring is a potentially big hurdle, except in the postprandial context. It is preferable to design devices, such as a Postprandial Feedback Meter, to continuously or noninvasively detect blood glucose and triglycerides from saliva, sweat, and tears such that the limit of detection is about 0.5 mg/mL—which is technically practical and useful.

Presently glucose levels detected using handheld or home glucose meters are not really useful for any immediate action to be taken by a patient. For instance, GlucoSuccess (Massachusetts General Hospital) for type 2 diabetics and prediabetics allows for entry of finger-stick glucose readings. But there is little to do with the readings other than research.

Noninvasive monitoring in accordance with the disclosed methods has the advantage of the natural integration of the data with a smartphone or other fitness focused electronic devices. Using a suitably anonymized data base of other users of such a device can provide a target of maintained glucose levels to each user to meet or exceed with each session of postprandial exercise. Such a target may be the best readings obtained by a user matched for age and the like in a last month, or over the course of a year or in a locality or zip code or even state or country etc. Even an average for such a grouping is a reasonable target to meet. One such implementation is illustrated in FIG. 9. Thus, the blood/plasma glucose levels are naturally and immediately affected by the actions taken by a user.

Advantageously, it is possible to include in the smartphone executable application a functionality for detecting a heart rate and blood flow. Preferably, the smartphone/health monitoring executable application communicates with a backend support facility to securely store patient data using the cellular phone network while providing anonymized data in the form of targets to motivate subjects and make postprandial exercising a competitive and pleasurable experience.

Throughout this application various publications/patents are referred to and the disclosures of these publications, all books and all patents and patent application publications referred to herein are hereby incorporated by reference in their entirety into the subject application to more fully describe the art to which the subject invention pertains.

It is apparent that the above embodiments and description and directives may be altered in many ways without departing from the scope of the invention. For example, many embodiments could use an appetite suppressant to further weight loss or bring about a greater change than without. Further, various aspects of a particular embodiment may contain patentable subject matter without regard to other aspects of the same embodiment. Still further, various aspects of different embodiments can be combined together. All references cited herein are incorporated herein by reference for all purposes. Accordingly, the scope of the invention should be interpreted in a manner consistent with these principles and in light of the claims.

We claim:

1. A post-prandial monitoring device for providing feedback to a subject to assist in adjusting glucose levels by way of postprandial exercise, the device comprising
an enzyme selected from a group consisting of glucose oxidase, glucose dehydrogenase, and glucose hexokinase for detecting a first glucose level in a first biological fluid sampled invasively;

a module for non-invasively detecting a second glucose level;

a display for showing the first glucose level in a first format and the second glucose level in a second format that is different from the first format;

wherein invasively detected glucose levels are communicated as concentrations and noninvasive glucose detection is communicated by way of a plurality of categories; and wherein upon measuring a second glucose level indicative of a postprandial state the device communicates one or more additional noninvasive glucose measurements suitable for measuring the effect of postprandial exercise and indicates the adequacy of the postprandial exercise based on the one or more additional measurements.

2. The post-prandial monitoring device of claim 1, wherein the categories are selected from a group consisting of a Low category encompassing a range of below about 75 mg/dL, a Desired category encompassing a range from about 70 mg/dL to about 130 mg/dL, or from about 70 mg/dL to about 120 mg/dL, or from about 70 mg/dL to about 100 mg/dL, a 'Moderately High' category encompassing a range from about 120 mg/dL to about 150 mg/dL, a 'Excellent' category encompassing glucose levels of about 70 mg/dL to about 85 mg/dL and the 'Too High' category encompassing glucose levels of about 150 mg/dL or higher.

3. The post-prandial monitoring device of claim 2 wherein the display when indicating the 'Low' category when reporting noninvasive glucose measurements also indicates an urgent need for checking glucose levels using invasive measurements.

4. The post-prandial monitoring device of claim 2, wherein a first noninvasive glucose test takes a time period selected from a group consisting of about 10 seconds, about 15 seconds, about 20 seconds, about 25 seconds, about 30 seconds, about 35 seconds, about 40 seconds, about 45 seconds, about 50 seconds, about 55 seconds, and about 60 seconds or more but less than about 2 minutes.

5. The post-prandial monitoring device of claim 2, the device comprising:

a first consumable strip for measuring blood/plasma glucose level; and a second consumable for non-invasive glucose level measurements.

6. The post-prandial monitoring device of claim 5, the device having a consumable with a triglyceride electrode for detecting triglycerides with a lipoprotein lipase and a glycerol oxidase providing an enzymatic part.

7. The post-prandial monitoring device of claim 5, the device further comprising:

a display or transmission facility for reporting a function of the difference—as a measure of glucose levels; and wherein the display indicates noninvasive glucose detection results as one of a plurality of categories instead of concentration units for glucose levels, and further flags glucose level falling below a threshold, or a reduction by a prescribed percent of a peak blood glucose level, or being within a category for the blood or plasma glucose level.

8. The post-prandial monitoring device of claim 7, wherein the device communicates to a smartphone results of measurements made using the device.

9. The post-prandial monitoring device of claim 7, wherein the device operates with a smartphone as a system to transmit anonymized results and comparisons and rankings with other comparable user's results on one or more of a group consisting of meal size control, glycemic control, and weight loss.

10. The post-prandial monitoring device of claim 2, the device comprising:

a single use consumable strip for measuring blood/plasma glucose level; and a single use consumable for non-invasive glucose level measurements using a biological fluid.

11. The post-prandial monitoring device of claim 10, the device having a consumable with an electrode having an enzymatic portion to provide a signal responsive to creatinine and creatine levels, an electrode having an enzymatic portion to provide a signal responsive to creatine levels in saliva, and an electrode lacking an enzymatic portion, to provide a reference signal for evaluating a glucose signal from the biological fluid.

* * * * *